(12) United States Patent
Detavernier et al.

(10) Patent No.: US 12,054,728 B2
(45) Date of Patent: Aug. 6, 2024

(54) ***BRASSICA* PLANT RESISTANT TO DOWNY MILDEW**

(71) Applicant: RIJK ZWAAN ZAADTEELT EN ZAADHANDEL B.V., De Lier (NL)

(72) Inventors: Mathieu Pierre Bertrand Detavernier, De Lier (NL); Martijn Doornbusch, De Lier (NL); Antje Ulrike Therese Klewer, De Lier (NL); Evgeny Novoselov, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

(21) Appl. No.: 17/482,624

(22) Filed: Sep. 23, 2021

(65) Prior Publication Data

US 2022/0090120 A1 Mar. 24, 2022

Related U.S. Application Data

(63) Continuation-in-part of application No. PCT/EP2020/058576, filed on Mar. 26, 2020.

(30) Foreign Application Priority Data

Mar. 26, 2019 (WO) .................. PCT/EP2019/057542

(51) Int. Cl.
*C12N 15/82* (2006.01)
*A01H 1/04* (2006.01)

(52) U.S. Cl.
CPC ......... *C12N 15/8282* (2013.01); *A01H 1/045* (2021.01)

(58) Field of Classification Search
None
See application file for complete search history.

(56) References Cited

U.S. PATENT DOCUMENTS 11,427,832 B2 8/2022 Suzuki et al.

OTHER PUBLICATIONS

Coelho et al. Acta Hortic.(2018) 1202 :93-100.*
Carlier et al. Plant Breeding (2012)131:170-175.*
Carlsson et al. Hereditas (2004)141:293-300.*
Farinho et al. Theor Appl Genet (2004) 109:1392-1398.*
Singh et al. Journal of Horticultural Science and Biotechnology (2012), 87(2):137-143.*
Neik Ting Xiang et al., Current Status and Challenges in Identifying Disease Resistance Genes in *Brassica napus*, Frontiers in Plant Science (2017) vol. 8, p. 1788.
Mohammed Akeel, et al., Resistances to Downy Mildew (*Hyaloperonospora brassicae*) in Diverse Brassicaceae Offer New Disease Management Opportunities for Oilseed and Vegetable Crucifer Industries, European Journal of Plant Pathology, (Oct. 26, 2018) Springer Netherlands, NL, vol. 153, No. 3.
J G Vicente, et al., Genetics of Resistance to Downy Mildew in *Brassica oleracea* and Breeding Towards Durable Disease Control for UK Vegetable Production, published online, Oct. 7, 2011, Plant Pathology, vol. 61, pp. 600-609.
International Search Report and Written Opinion dated Jun. 5, 2020 in Int'l Application No. PCT/EP2020/058576.
P. Coelho, et al., The Relationship Between Cotyledon and Adult Plant Resistance to Downy Mildew (*Peronospora parasitica*) in *Brassica oleracea*, Proc. Int. Symp. on Brassicas. Eds. Thomas Gregoire & Antonio A. Monteiro, Acta Hort. 459, ISHS (1998).
Paula S. Coelho, et al., Inheritance of downy mildew resistance in mature broccoli plants, Euphytica (2003) 131:65-69.

* cited by examiner

*Primary Examiner* — Medina A Ibrahim
(74) *Attorney, Agent, or Firm* — Duane Morris LLP; Thomas J. Kowalski

(57) ABSTRACT

The invention relates to a *Brassica* plant that is resistant to *Hyaloperonospora brassicae*, which plant may comprise a QTL on chromosome 8, and optionally a QTL on chromosome 4, and/or a QTL on chromosome 1. The presence of the QTL on chromosome 8 can be identified by use of at least one of the markers selected from the group consisting of SEQ ID NOS: 1 to 7; the presence of the QTL on chromosome 4 can be identified by use of at least one of the markers selected from the group consisting of SEQ ID NOS: 8 to 16; and the presence of the QTL on chromosome 1 can be identified by use of at least one of the markers selected from the group consisting of SEQ ID NOS: 17 to 22. The QTL is as comprised in the genome of a *Brassica* plant representative seed of which was deposited with the NCIMB under accession number NCIMB 43346.

41 Claims, 3 Drawing Sheets
Specification includes a Sequence Listing.

Figure 1 – Marker sequences SEQ ID Nos. 1-22

SEQ ID No. 1
ACCCTTTTGAGCTGAGCGGATAATTCATCATAAACGGCACCGTTTTACTGAATGGGTGTTTGGTTAC
ACGTGTACTAGTATTCGAGAGAGGAGTAGAAARGCGCTAATCTGATGTTGATAAGCAAATTATATTT
TATGTTTAGCTATCAACATCATACTAAACTTGCCAGATGACTCTGTATTGCATAATACCAMARTAAT

SEQ ID No. 2
AAGAATCATTGAGCCAATGTCGCTTGGAAATCCTGTCAAGAGAAATAAAGATCTGTTACTCACAAAT
GAAGACAAATACATTATCGTTACATGTGAAACATAATTTGTCTTACCTCCTTTATTAAATACGCTACC
GACATAGAACATAACCCCTGAGCTTCCAGAGAGCTGTTGCAGAAGCATTAGCCCCACACCAATCTG

SEQ ID No. 3
TGTTGGTCATCTTGCATCTCCATTGGATCCTCGTTTTCCTCTCTTGCATCCATCTCTAGGAGTACTTTT
CCCTTCACTTCCTACTGAAAAACCATTGWTAACCAAAACAGTCAGTTACAAGTTTAAATAAYTGGTC
GTCCACGCGTAGAAGCTAACAAGTACATGTGTGCATAAACCGTATCAGGCATTTATTTATAAAGA

SEQ ID No. 4
TAGGATTTGTTCTCAATGTGACCGGAAGTTACACCACTATGTGACTATGGATAGTCCCGATCACTCG
CGGCTTCTGTTGTGCGAAAAATGCGTTTCGCAGACCGCAGATGTCCAGTGCCTTGAGCAAGGATTGT
GCCTATGCCAAACATGCGTTCCAAACGCCACCGTCACCTCACGTTTTCCTTTTTGTAACGTTTCTAA

SEQ ID No. 5
TGACAGCAATTACTTACATCACTGGATAATGGTTTCTCGCTGTTTTTCACTTAATTAGGTKAGTAAAA
GGAAAACCAAAACGGCAAAATAGATTTAAGAACAAGAGAGAACAAAGATAAGTKAAACACGAGTG
ATTGGGAACCAATTTGACCCGCAAGTTTTGGCGTAACCAAACAACTCGCACCAAMAAGATTTTATCT
T

SEQ ID No. 6
GGCCTATGTTGGGCCTCTTAAGCCCGTAGTTTGATAAGCTTCCAAGAACCAGCCATGATAAGAGCAG
TATAAGCTTGTCTACTAGCCATAGAGGTAGCCACTTCATTAACATCACTGAGATTCCGAATGTTGACT
TTCCCATAACTTCTCTAGGTAACACATGAACCTGGTCGAATTAAGAAACACAAGAACATGGTTAGC

SEQ ID No. 7
ACTCAAGTGTGACMCACATTAAACCWTATCACGACATACATGGATCCCGCGAGAACAGATATGGAA
ATTCTAATGGGATGAGACCATATATTTGACAATATTGTTCTCTRTAAGGTYGTGATGTAAGGAGCAG
TATCTCTTCAGGTTTATTAACAACACTATGATAAGTATTATGAGAAACAAACTAAGCAGGCTTTGTTC

SEQ ID No. 8
TCTACCTCAAGTTGAAGAATTTCTGACACGTTCAGAATTTGTGCTCAGTAAGTTCTCATGAATCATGA
TATATTCTATCTTTATATTCAATACGACTTTGAACTTACCCCyATAAGTCCCAGCTTTTTGAATTATC
TTTCGTCAAATATCTTTGTTGTTTTCTAAGTTGTGTCAACCACCTGTTTGCAGCAAATGAACCA

SEQ ID No. 9
AGTCACGTGGCTTGATAATGGTACTACCTTCACNGATCGCCAATGAGAGTTGGACCAACGAACAGA
ATCCAGATCACTGATACCAGTTATAGTACCCATGTACCTGCAG

SEQ ID No. 10
AATTTAACAAAGCAACATGCAAAGGAATATTATTTTTTTGGCATCATTCACTTCAAGGATGAGAAGG
GAAAGGAGGCCATTTCCCAAACTTAGGGTGTGGGATGTATTTAGGTGGGAAAGGCGGAAGCTTCGG

Fig. 1 continued

AAGTGGTGGACACGGTTTCTTTGGAATCACCACTGGTGGCTTGTAGATTGGTTTGTATATGGGCACC
G

SEQ ID No. 11
AGATTGAGATATTCCAACGCAGAAAAGTTTGCAAGATATGCAGGTATACTTCCAAAGAGACTATTAT
TGGAGAAATCAACTTCTACAAGACCCTTTAACCTTTGTATATCCGGAAAGGCTCCATCGAAACGATT
TCCTTGCAGCAAAAGTGTTTCCAAGGAGAGACAGTTTCCCAAAGTTTGTGGAAGTTGTCCGGATAAT

SEQ ID No. 12
TTTGATGATATTATGAATTGGTTGGCTAAATATGCTTGGAAAACTATATGAATGTTGGTATAAATTG
TCGCAGGAACTACCAGTTAATCAAAGAGCTGACACGGTGAATAGTCTGGTTTTTGAAGCAAACGCA
CGAGTTAGAGATCCGGTATATGGCTGCGTAGGAGCAATCTCCTACTTACAAAACCAAGTCTCACAGC
T

SEQ ID No. 13
GAAGAGCTAGGATGATGCGGGTGATGAACAGAGGGGATTCTCAGAAACAGTGCAAATAAAGGGCA
ATACGCCCGGGAAAGGGAAGGAGTAAAACAAGCTGTTCCCAGCATAACTCTGAATCTGTTGTACAT
TCAATTTTCAATACAATTCATCTGCAAGAGACAGGGGAAACACATTCATGAAGGTATATCAAGAATT
ACA

SEQ ID No. 14
CCATCAACCCTTTAGCAAACGGATACATATGAGTCAATACCCACATGCTAAAGAACGTCCCTCCTAG
CAACTTGTTCCACTGCGGAATCACACTATATATAGTCCTCGAAGCTCCTATCACAATCGCAACGAGG
TTCACTACAATGATCGTTAGAGGCATGATGAACAACCCCGTCCACTTCACAATGTAAAGATCCGCAA

SEQ ID No. 15
TCCACATCTTTTGTTNACTGAGATTAGTCCCTTTTGGCAGAATTGGTATTGTGCATCAAAAACACAAG
CAGAAAGTGAAGCTTTCGAATTTGCAAAACGAACCGGGATTAGTCTCGTCAGC

SEQ ID No. 16
TCTTTCGTTTTAGATAATGCAGCTTACATCGATCTGGAAGCGCATAGAATATGCCTCGTGAAACCTC
GTCTTTCGCAAGGAATTCTATAGATTCCCAGTAAAGGGGGCTCTTAAGAACCAACCCATTGACCTCC
CCTACTCGGATAACAAGAACGGCCATTCTCTCTTCCATCGATTGTTGGGATCGAAAACATTCATTAG

SEQ ID No. 17
AAACTTAATTAAATACTGGAAACAACACTCTGGAACAAGAACGTGTTGAGTATCTTTAACACACATG
TCTGAAGATACGTTTTCACCAAGTTTTGCCATCGTGGGAATAACGTGGAGTTGGAGAGAGGGAGAG
GAGTTTAAAATGTTTGAAGTATGGCTTAAATCTCGTATATCAGTGTGCTTTGTTGGCTTGTGTTCTGT

SEQ ID No. 18
CAGAGAACTGGGCAACCTTGGCCTCCTTTGTGAAATTCCTTTTAAACGAACAAAAAGTATCTTTCTC
TGGCCTGGTTTGAGCCCATCCACCATGGAAGGGATTGACCTTTGAAGATCCGCCATGGAGAATAAG
ATAAGTTCTTTGTTTACGAAATCACTGAAGGAAATTTTCTGTTGCTTCTGATCAAGATGAGTGCCAG

SEQ ID No. 19
CCGGATRTTAACCAGTACCGGTTATATCCGAGTTAATATCATCATCTTCTTCTTCAGCTACTCTGGTA
TGAAGCTGGATCCCGCAAGAGAGATCTTGTAAAARTGCAGAGAGACCAGAAGTCTATGTGATTCGT
TCGGACATTCCGACAAGAAGCGATGTCGAGGAGCTGTCGGCTTCTCCTCTCCCGCGYTTCACTCTGT

SEQ ID No. 20

Fig. 1 continued

CTGGACTAATGCTGACTTCTCCTCTTAGTCAACTTAATAGCGTCAGTGTTTCTAATTTTCCACTGTTG
CGGCCTCAAGATCTTAGGTACTAAATAACTTCATACAGGTTATCCTTTGATTTGTTTATCTAACATTC
GGTTTTATGATGATTGAAGGTTGGCTATTGCGGCTGCTGAAAGGCTGTTGATTTTGGAACCTCTT

SEQ ID No. 21
AGAGCACAGCTTCTAGAAAGACAGGTGGATGATCTAGAAGACTGCTGTGGATAAGGAATAAAGAAT
AACACCTGAGGAGCAAAGGGGGAACATATCACGTCCTGCTACGGTCTCTTAACCACGGGTGACGAG
CTGTGGTTGGCTAGTGGTCATTTCCTATATAAGCTCTAGTCTATCTTTGTAATAGGTATCGAGTATTT
G

SEQ ID No. 22
GAGTCTTGTGTTGGAGAAACACTTTCACTTAGCATTGAGCCCATCACAAGTGATGCTATTGAGACAG
GTCCAACTGCAAGATGCTTTGAACTCCCAAGAACTGAGTATATAAGTGGTGGCACAAAGCTTGAATC
TGCATGCAACCACCAAATTTATTAATTAGAGTCAGGTTTAGTTAATTATACTGATTAGTCTAATTAG

SEQUENCE LISTING

```
<160> NUMBER OF SEQ ID NOS: 22

<210> SEQ ID NO 1
<211> LENGTH: 201
<212> TYPE: DNA
<213> ORGANISM: Brassica oleracea
<220> FEATURE:
<223> OTHER INFORMATION: Marker

<400> SEQUENCE: 1
acccttttga gctgagcgga taattcatca taaacggcac cgttttactg aatgggtgtt     60
tggttacacg tgtactagta ttcgagagag gagtagaaar gcgctaatct gatgttgata    120
agcaaattat attttatgtt tagctatcaa catcatacta aacttgccag atgactctgt    180
attgcataat accamartaa t                                              201

<210> SEQ ID NO 2
<211> LENGTH: 201
<212> TYPE: DNA
<213> ORGANISM: Brassica oleracea
<220> FEATURE:
<223> OTHER INFORMATION: Marker

<400> SEQUENCE: 2
aagaatcatt gagccaatgt cgcttggaaa tcctgtcaag agaaataaag atctgttact     60
cacaaatgaa gacaaataca ttatcgttac atgtgaaaca taatttgtct tacctccttt    120
attaaatacg ctaccgacat agaacataac ccctgagctt ccagagagct gttgcagaag    180
cattagcccc acaccaatct g                                              201

<210> SEQ ID NO 3
<211> LENGTH: 201
<212> TYPE: DNA
<213> ORGANISM: Brassica oleracea
<220> FEATURE:
<223> OTHER INFORMATION: Marker

<400> SEQUENCE: 3
```

```
tgttggtcat cttgcatctc cattggatcc tcgttttcct ctcttgcatc catctctagg    60 agtactttc ccttcacttc ctactgaaaa accattgwta accaaaacag tcagttacaa   120
gtttaaataa ytggtcgtcc acgcgtagaa gctaacaagt acatgtgtgc ataaaccgta   180
tcaggcattt atttataaag a                                            201
```

<210> SEQ ID NO 4
<211> LENGTH: 201
<212> TYPE: DNA
<213> ORGANISM: Brassica oleracea
<220> FEATURE:
<223> OTHER INFORMATION: Marker

<400> SEQUENCE: 4

```
taggatttgt tctcaatgtg accggaagtt acaccactat gtgactatgg atagtcccga    60
tcactcgcgg cttctgttgt gcgaaaaatg cgtttcgcag accgcagatg tccagtgcct   120
tgagcaagga ttgtgcctat gccaaacatg cgttccaaac gccaccgtca cctcacgttt   180
tcctttttgt aacgtttcta a                                            201
```

<210> SEQ ID NO 5
<211> LENGTH: 201
<212> TYPE: DNA
<213> ORGANISM: Brassica oleracea
<220> FEATURE:
<223> OTHER INFORMATION: Marker

<400> SEQUENCE: 5

```
tgacagcaat tacttacatc actggataat ggtttctcgc tgttttcac ttaattaggt     60 kagtaaaagg aaaaccaaaa cggcaaaata gatttaagaa caagagagaa caaagataag   120
tkaaacacga gtgattggga accaatttga cccgcaagtt ttggcgtaac caaacaactc   180
gcaccaamaa gattttatct t                                            201
```

<210> SEQ ID NO 6
<211> LENGTH: 201
<212> TYPE: DNA
<213> ORGANISM: Brassica oleracea
<220> FEATURE:
<223> OTHER INFORMATION: Marker

<400> SEQUENCE: 6

```
ggcctatgtt gggcctctta agcccgtagt ttgataagct tccaagaacc agccatgata    60
agagcagtat aagcttgtct actagccata gaggtagcca cttcattaac atcactgaga   120
ttccgaatgt tgactttccc ataacttctc taggtaacac atgaacctgg tcgaattaag   180
aaacacaaga acatggttag c                                            201
```

<210> SEQ ID NO 7
<211> LENGTH: 201
<212> TYPE: DNA
<213> ORGANISM: Brassica oleracea
<220> FEATURE:
<223> OTHER INFORMATION: Marker

<400> SEQUENCE: 7

```
actcaagtgt gacmcacatt aaaccwtatc acgacataca tggatcccgc gagaacagat    60
atggaaattc taatgggatg agaccatata tttgacaata ttgttctctr taaggtygtg   120
atgtaaggag cagtatctct tcaggtttat taacaacact atgataagta ttatgagaaa   180
```

```
caaactaagc aggctttgtt c                                              201
```

<210> SEQ ID NO 8
<211> LENGTH: 201
<212> TYPE: DNA
<213> ORGANISM: Brassica oleracea
<220> FEATURE:
<223> OTHER INFORMATION: Marker

<400> SEQUENCE: 8

```
tctacctcaa gttgaagaat ttctgacacg ttcagaattt gtgctcagta agttctcatg    60
aatcatgata tattctatct ttatattcaa tacgactttg aacttacccc cyataagtcc   120
cagcttttg  aattatcttt cgtcaaatat ctttgttgtt ttctaagttg tgtcaaccac   180
ctgtttgcag caaatgaacc a                                              201
```

<210> SEQ ID NO 9
<211> LENGTH: 109
<212> TYPE: DNA
<213> ORGANISM: Brassica oleracea
<220> FEATURE:
<223> OTHER INFORMATION: Marker
<220> FEATURE:
<221> NAME/KEY: misc_feature
<222> LOCATION: 34
<223> OTHER INFORMATION: /note="n = a or c or t or g"

<400> SEQUENCE: 9

```
agtcacgtgg cttgataatg gtactacctt cacngatcgc caatgagagt tggaccaacg    60
aacagaatcc agatcactga taccagttat agtacccatg tacctgcag              109
```

<210> SEQ ID NO 10
<211> LENGTH: 201
<212> TYPE: DNA
<213> ORGANISM: Brassica oleracea
<220> FEATURE:
<223> OTHER INFORMATION: Marker

<400> SEQUENCE: 10

```
aatttaacaa agcaacatgc aaaggaatat tatttttttg gcatcattca cttcaaggat    60
gagaagggaa aggaggccat ttcccaaact tagggtgtgg gatgtattta ggtgggaaag   120
gcggaagctt cggaagtggt ggacacggtt tctttggaat caccactggt ggcttgtaga   180
ttggtttgta tatgggcacc g                                              201
```

<210> SEQ ID NO 11
<211> LENGTH: 201
<212> TYPE: DNA
<213> ORGANISM: Brassica oleracea
<220> FEATURE:
<223> OTHER INFORMATION: Marker

<400> SEQUENCE: 11

```
agattgagat attccaacgc agaaaagttt gcaagatatg caggtatact tccaaagaga    60
ctattattgg agaaatcaac ttctacaaga ccctttaacc tttgtatatc cggaaaggct   120
ccatcgaaac gatttccttg cagcaaaagt gtttccaagg agagacagtt tcccaaagtt   180
tgtggaagtt gtccggataa t                                              201
```

<210> SEQ ID NO 12
<211> LENGTH: 201
<212> TYPE: DNA
<213> ORGANISM: Brassica oleracea -continued

```
<220> FEATURE:
<223> OTHER INFORMATION: Marker

<400> SEQUENCE: 12
tttgatgata ttatgaattg gttggctaaa tatgcttgga aaactatatg aatgttggta    60
taaattgtcg caggaactac cagttaatca aagagctgac acggtgaata gtctggtttt  120
tgaagcaaac gcacgagtta gagatccggt atatggctgc gtaggagcaa tctcctactt  180
acaaaaccaa gtctcacagc t                                             201

<210> SEQ ID NO 13
<211> LENGTH: 201
<212> TYPE: DNA
<213> ORGANISM: Brassica oleracea
<220> FEATURE:
<223> OTHER INFORMATION: Marker

<400> SEQUENCE: 13
gaagagctag gatgatgcgg gtgatgaaca gaggggattc tcagaaacag tgcaaataaa    60
gggcaatacg cccgggaaag ggaaggagta aaacaagctg ttcccagcat aactctgaat   120
ctgttgtaca ttcaattttc aatacaattc atctgcaaga gacaggggaa acacattcat   180
gaaggtatat caagaattac a                                             201

<210> SEQ ID NO 14
<211> LENGTH: 201
<212> TYPE: DNA
<213> ORGANISM: Brassica oleracea
<220> FEATURE:
<223> OTHER INFORMATION: Marker

<400> SEQUENCE: 14
ccatcaaccc tttagcaaac ggatacatat gagtcaatac ccacatgcta agaacgtcc     60 ctcctagcaa cttgttccac tgcggaatca cactatatat agtcctcgaa gctcctatca   120
caatcgcaac gaggttcact acaatgatcg ttagaggcat gatgaacaac cccgtccact   180
tcacaatgta aagatccgca a                                             201

<210> SEQ ID NO 15
<211> LENGTH: 121
<212> TYPE: DNA
<213> ORGANISM: Brassica oleracea
<220> FEATURE:
<223> OTHER INFORMATION: Marker
<220> FEATURE:
<221> NAME/KEY: misc_feature
<222> LOCATION: 16
<223> OTHER INFORMATION: /note="n = a or c or t or g"

<400> SEQUENCE: 15
tccacatctt ttgttnactg agattagtcc cttttggcag aattggtatt gtgcatcaaa    60
aacacaagca gaaagtgaag ctttcgaatt tgcaaaacga accgggatta gtctcgtcag   120
c                                                                   121

<210> SEQ ID NO 16
<211> LENGTH: 201
<212> TYPE: DNA
<213> ORGANISM: Brassica oleracea
<220> FEATURE:
<223> OTHER INFORMATION: Marker

<400> SEQUENCE: 16
```

```
tctttcgttt tagataatgc agcttacatc gatctggaag cgcatagaat atgcctcgtg    60
aaacctcgtc tttcgcaagg aattctatag attcccagta aaggggggctc ttaagaacca   120 acccattgac ctcccctact cggataacaa gaacggccat tctctcttcc atcgattgtt   180
gggatcgaaa acattcatta g                                              201

<210> SEQ ID NO 17
<211> LENGTH: 201
<212> TYPE: DNA
<213> ORGANISM: Brassica oleracea
<220> FEATURE:
<223> OTHER INFORMATION: Marker

<400> SEQUENCE: 17
aaacttaatt aaatactgga acaacactc tggaacaaga acgtgttgag tatctttaac     60
acacatgtct gaagatacgt tttcaccaag ttttgccatc gtgggaataa cgtggagttg   120
gagagaggga gaggagttta aaatgtttga agtatggctt aaatctcgta tatcagtgtg   180
ctttgttggc ttgtgttctg t                                              201

<210> SEQ ID NO 18
<211> LENGTH: 201
<212> TYPE: DNA
<213> ORGANISM: Brassica oleracea
<220> FEATURE:
<223> OTHER INFORMATION: Marker

<400> SEQUENCE: 18
cagagaactg ggcaaccttg gcctcctttg tgaaattcct tttaaacgaa caaaaaagta    60 tcttctctg gcctggtttg agcccatcca ccatggaagg gattgacctt tgaagatccg   120
ccatggagaa taagataagt tctttgttta cgaaatcact gaaggaaatt ttctgttgct   180
tctgatcaag atgagtgcca g                                              201

<210> SEQ ID NO 19
<211> LENGTH: 201
<212> TYPE: DNA
<213> ORGANISM: Brassica oleracea
<220> FEATURE:
<223> OTHER INFORMATION: Marker

<400> SEQUENCE: 19
ccggatrtta accagtaccg gttatatccg agttaatatc atcatcttct tcttcagcta    60
ctctggtatg aagctggatc ccgcaagaga gatcttgtaa aartgcagag agaccagaag   120
tctatgtgat tcgttcggac attccgacaa gaagcgatgt cgaggagctg tcggcttctc   180
ctctcccgcg yttcactctg t                                              201

<210> SEQ ID NO 20
<211> LENGTH: 201
<212> TYPE: DNA
<213> ORGANISM: Brassica oleracea
<220> FEATURE:
<223> OTHER INFORMATION: Marker

<400> SEQUENCE: 20
ctggactaat gctgacttct cctcttagtc aacttaatag cgtcagtgtt tctaattttc    60
cactgttgcg gcctcaagat cttaggtact aaataacttc atacaggtta tcctttgatt   120
tgtttatcta acattcggtt ttatgatgat tgaaggttgg ctattgcggc tgctgaaagg   180
ctgttgattt tggaacctct t                                              201
```

```
<210> SEQ ID NO 21
<211> LENGTH: 201
<212> TYPE: DNA
<213> ORGANISM: Brassica oleracea
<220> FEATURE:
<223> OTHER INFORMATION: Marker

<400> SEQUENCE: 21
agagcacagc ttctagaaag acaggtggat gatctagaag actgctgtgg ataaggaata        60
aagaataaca cctgaggagc aaaggggaa catatcacgt cctgctacgg tctcttaacc       120
acgggtgacg agctgtggtt ggctagtggt catttcctat ataagctcta gtctatcttt       180
gtaataggta tcgagtattt g                                                 201

<210> SEQ ID NO 22
<211> LENGTH: 201
<212> TYPE: DNA
<213> ORGANISM: Brassica oleracea
<220> FEATURE:
<223> OTHER INFORMATION: Marker

<400> SEQUENCE: 22
gagtcttgtg ttggagaaac actttcactt agcattgagc ccatcacaag tgatgctatt        60
gagacaggtc caactgcaag atgctttgaa ctcccaagaa ctgagtatat aagtggtggc       120
acaaagcttg aatctgcatg caaccaccaa atttattaat tagagtcagg tttagttaat       180
tatactgatt agtctaatta g                                                 201
```

BRASSICA PLANT RESISTANT TO DOWNY MILDEW

RELATED APPLICATIONS AND INCORPORATION BY REFERENCE

This application is a continuation-in-part application of international patent application Serial No. PCT/EP2020/058576 filed Mar. 26, 2020, and published as International Publication No. WO 2020/193712 on Oct. 1, 2020, which claims benefit of PCT international application Serial Nos. PCT/EP2019/057542 filed Mar. 26, 2019 and PCT/EP2019/060512 filed Apr. 24, 2019.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE STATEMENT

The instant application contains a Sequence Listing which has been submitted electronically and is hereby incorporated by reference in its entirety. Said ASCII copy is named Y795400509SL.txt and is 9 kbytes in size.

FIELD OF THE INVENTION

The present invention relates to a *Brassica* plant, in particular a *Brassica oleracea* plant, that is resistant to *Hyaloperonospora brassicae*. The invention further relates to progeny, seed and a part of the *Brassica* plant that is resistant to *Hyaloperonospora brassicae* and to a food product which may comprise such part of the *Brassica* plant. The invention also relates to propagation material suitable for producing the *Brassica* plant, to a marker for the identification of resistant *Brassica* plants, to use of the said marker to identify and/or develop a *Hyaloperonospora brassicae* resistant *Brassica* plant or other markers, to a method of selecting a *Brassica* plant for the resistance and to a method for producing a *Hyaloperonospora brassicae* resistant *Brassica* plant.

BACKGROUND OF THE INVENTION

*Brassica* is a genus of plants, taxonomically embedded within the Brassicaceae family. It contains many economic important crops that serve as a source of food, but species are also employed in the production of oil. In general, the *Brassica* genus includes *B. napus, B. nigra, B. rapa, B. juncea* and *B. oleracea. Brassica napus* is very important in the production of vegetable oil that is increasingly applied in the fuel industry. Together with *Brassica rapa, Brassica nigra* and *Brassica juncea, Brassica oleracea* is a species that plays a very important role in the production of human food. Over time, cultivars originated within *B. oleracea* amongst which cabbage, cauliflower, collards, broccoli, kohlrabi and Brussels sprouts can be found.

Wild, undomesticated *Brassica oleracea* has been bred into a broad range of different horticultural cultivars that remained sexually compatible. However, their appearance does not show a very high level of phylogenetic similarity. The wide range in differences of morphological characteristics within *Brassica oleracea* has long been of interest and form the foundation of a cultivars' uniqueness. These include an enlarged inflorescence (cauliflower, broccoli); an enlarged stem (kohlrabi); an enlarged apical bud (cabbage); and enlarged lateral buds (Brussels' sprouts).

Breeding of cruciferous vegetables like *Brassica oleracea* varieties aims at the production of commercial varieties optimally adapted to local growing conditions which allows the grower to maximize the productivity of high quality plants. Many characteristics need to be taken into account during selection which relate to both input as well as output traits. One of the most important input traits in this respect relates to disease resistance, in particular to resistance towards micro-organisms.

*Brassica* plants are affected by a wide range of pests and diseases. These threats are therefore high priority objects for *Brassica* breeders, in order to obtain crops that are vigorous and highly resistant. In absence of resistances in these crops, growers necessarily have to apply agronomic strategies like crop rotation or use fungicides, in order to reduce pest damage in areas where cruciferous vegetables are grown.

Downy mildew—in *Brassica* plants caused by the oomycete *Hyaloperonospora brassicae*—is a common, probably the most damaging, disease found among broccolis, cauliflowers and other plants belonging to the Brassicaceae family. Downy mildew is caused by different isolates of *Hyaloperonospora brassicae*. The obligate parasite lives on *Brassica* plants and the symptoms of the infection appear primarily on the aerial parts of the plants. Symptoms of the disease, such as necrotic spots with yellow or brown edges, and optionally also sporulation, can destroy the quality of the leaves, stems and of the plant head.

Infection by *Hyaloperonospora brassicae* (Gäum.) Göker, Voglmayr, Riethm Weiss & Oberw. 2003, occurs worldwide. Cultural practices and/or chemical treatments have been unsuccessful in protecting crops or have proven to be too expensive. Therefore, the development of resistant cultivars is now considered the most economical and efficient method for the control of downy mildew.

As for oomycetes like *Hyaloperonospora brassicae* it is known that they continuously develop the ability to break resistances present in their host plant, new resistance loci are very valuable assets. Therefore a *Brassica* having a broad resistance to *Hyaloperonospora brassicae* is preferred.

Plants can be resistant to *Hyaloperonospora brassicae* at seedling stage and/or at adult plant stage. If the plants are not resistant to *Hyaloperonospora brassicae* at seedling stage, the cotyledons or young plants can be infected and show the symptoms of a susceptible plant. The infection at this stage can lead to mature plants that have heads and/or leaves that are not properly developed or it can even lead to the death of the infected plants. The infection at seedling stage thereby leads to reduced yield or to reduced quality of the plant heads or leaves. Therefore a *Brassica* resistant to *Hyaloperonospora brassicae* at all plant stages, i.e. at seedling stage and adult plant stage, or at least the cotyledon stage, is preferred.

Citation or identification of any document in this application is not an admission that such document is available as prior art to the present invention.

SUMMARY OF THE INVENTION

Summarizing, there is a need for a reliable resistance towards *Hyaloperonospora brassicae* at all plant stages. In particular, a resistance towards multiple isolates of *Hyaloperonospora brassicae* at all plant stages is preferred.

It is the object of the present invention to provide *Hyaloperonospora brassicae* resistant *Brassica* plants, in particular *Brassica oleracea* plants, in which the resistance is improved as compared to existing *Hyaloperonospora brassicae* resistant *Brassica* plants. "Improved" in this context includes, but is not limited to, resistance already in the cotyledon stage and/or broad resistance. "Improved" also refers to a higher level of resistance as compared to another plant.

This object is met by the *Brassica* plants of the invention, which are resistant already in the cotyledon stage, and to multiple isolates, i.e. at least 3 isolates, of *Hyaloperonospora brassicae.*

In the research that led to the present invention, novel *Brassica* plants were developed that are resistant against *Hyaloperonospora brassicae*. It was determined that the resistance of the invention is controlled by a QTL on chromosome 8, which can be combined with a QTL on chromosome 4 and/or a QTL on chromosome 1 in order to increase the resistance.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

The Deposits with NCIMB Ltd. (Ferguson Building, Craibstone Estate, Bucksburn, Aberdeen, AB21 9YA), under deposit accession number NCIMB 43346 were made and accepted pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

Seeds of a *Brassica oleracea* var. *italica* Plenck plant which may comprise the QTL of the invention on chromosome 8, the QTL of the invention on chromosome 4 and the QTL of the invention on chromosome 1, which confer resistance to *Hyaloperonospora brassicae*, were deposited under accession number NCIMB 43346 on Feb. 4, 2019 with NCIMB Ltd. (Ferguson Building, Craibstone Estate, Bucksburn, Aberdeen, AB21 9YA). All seeds of the deposit comprise the QTL on chromosome 8, the QTL on chromosome 4 and the QTL on chromosome 1 homozygously. Plants grown from these seeds show thus resistance against *Hyaloperonospora brassicae.*

The deposited seeds do not meet the DUS criteria which are required for obtaining plant variety protection, and can therefore not be considered to be plant varieties.

BRIEF DESCRIPTION OF THE DRAWINGS

The following detailed description, given by way of example, but not intended to limit the invention solely to the specific embodiments described, may best be understood in conjunction with the accompanying drawings.

FIG. 1: Genomic sequences of SEQ ID NOS: 1 to 22 that can be used as markers, or can be used to develop markers, for the identification of a QTL of the invention.

DETAILED DESCRIPTION OF THE INVENTION

As used herein, a *Brassica* plant is "susceptible" when it does not comprise the QTL of the invention on chromosome 8. The susceptible plant preferably does not comprise the QTL of the invention on chromosome 4 and/or the QTL of the invention on chromosome 1. A susceptible plant scores 8-9, when assessed using the scores of Table 1. A "wild type plant" as used herein is a susceptible *Brassica* plant.

As used herein, "resistance to *Hyaloperonospora brassicae*", "resistance against *Hyaloperonospora brassicae*", "showing resistance to *Hyaloperonospora brassicae*" or "resistance of the invention" is defined as the capacity of a plant to resist infection in all plant stages by all or most, but at least three, isolates of *Hyaloperonospora brassicae*, preferably to resist isolates herein called "isolate 1", "isolate 2" and "isolate 3", in the cotyledon stage, defining a "broad resistance". "Isolate 1" and "isolate 2" are *Hyaloperonospora brassicae* isolates that were collected in The Netherlands, "isolate 2" was collected in Fijnaart. "Isolate 3" was collected in Rommelshausen, Germany. The plants are visually phenotyped in the cotyledon stage to identify a *Hyaloperonospora brassicae* resistant plant. Resistance is suitably scored on a scale as represented in Table 1 (scores 1-7). "Resistance" includes also "increased resistance", which is intended to mean that the plant has a higher resistance level and has a score as presented in Table 1 that is lower than the score of the *Brassica* plant to which it is compared. The plant that has a higher resistance level shows less necrotic spots and/or sporulation than the plant to which it is compared.

*Brassica* plants which may comprise the QTL of the invention on chromosome 8 preferably in a homozygous state are resistant.

*Brassica* plants which may comprise the QTL of the invention on chromosome 8 homozygously and the QTL of the invention on chromosome 4 homozygously or the QTL of the invention on chromosome 1 homozygously, have an increased resistance to *Hyaloperonospora brassicae*, as compared to a plant which may comprise only the QTL of the invention on chromosome 8.

*Brassica* plants which may comprise the QTL of the invention on chromosome 8 homozygously and the QTL of the invention on chromosome 4 homozygously and the QTL of the invention on chromosome 1 heterozygously, and *Brassica* plants which may comprise the QTL of the invention on chromosome 8 homozygously and the QTL of the invention on chromosome 4 heterozygously and the QTL of the invention on chromosome 1 homozygously, have an increased resistance to *Hyaloperonospora brassicae*, as compared to a plant which may comprise only the QTL of the invention on chromosome 8 homozygously and the QTL of the invention on chromosome 4 or the QTL of the invention on chromosome 1 homozygously.

The highest resistance level is shown by *Brassica* plants which may comprise the QTL of the invention on chromosome 8, the QTL of the invention on chromosome 4 and the QTL of the invention on chromosome 1, all three QTLs in a homozygous stage.

Other examples of different combinations of the QTLs of the invention on chromosome 8, 4 and 1 and the averages of their resistance levels are shown in Table 4. The *Brassica* plant of the invention is preferably a *Brassica oleracea* plant, but can also be any other plant of the genus *Brassica* into which the skilled person can introgress the genetic information of the invention, e.g. at least the following *Brassica* species: *Brassica oleracea, Brassica napus, Brassica campestris, Brassica cretica, Brassica rapa, Brassica juncea,* and *Brassica nigra.* The skilled person knows how to make interspecific crosses with these species, e.g. by means of embryo rescue, protoplast fusion, and other related technologies. The *Brassica* plant of the invention can also be any plant of the genus *Brassica* into which the QTL(s) of the invention can be introduced by other means, such as for instance by mutagenesis or genetic modification. The invention relates in particular to *Brassica oleracea* plants of the following crop types:

convar. *acephala* (DC.) Alef. (kales)
convar. *botrytis* (L.) Alef. Var. *botrytis* (cauliflower, romanesco)
convar. *capitata* (L.) Alef. (cabbage)
convar. *capitata* (L.) Alef. Var. *alba* DC. (white cabbage)
convar. *capitata* (L.) Alef. Var. *rubra* (L.) Thell. (red cabbage), also called convar. *capitata* (L.) Alef. Var. *Rubra* DC.
convar. *capitata* (L.) Alef. Var. *sabauda* L. (savoy cabbage), also called convar. *capitata* (L.) Alef. Var. *sabauda* DC. convar. *gemmifera* Zenker (brussels sprouts), also called var. *gemmifera* DC.
var. *gongylodes* L. (kohlrabi) also called convar. *acephala* (DC.) Alef. Var. *gonglylodes* L.
var. *italica* Plenck. (broccoli, calabrese), broccoli also called convar. *botrytis* (L.) Alef. var. *cymosa* Duch.
convar. *acephala* (DC.) Alef. var. *sabellica* L. (borecale)
convar. *acephala* (DC.) Alef. var. *viridis* L. (collards)
var. *alboglabra* (L. H. Bailey) Musil (Chinese kale)
var. *chinensis* Prain (burma sarson)
var. *fimbriata* Mill. (kitchen kale)
var. *fruticosa* Metz. (thousand-head kale)
var. *tronchuda* L. H. Bailey (tronchuda cabbage)
var. *costata* (Portugese cabbage)
var. *medullosa* (marrow stem kale)
var. *palmifolia* (kale, Jersey kale)
var. *ramosa* (thousand-head kale)

Preferred are the crop types broccoli, cauliflower, romanesco, red cabbage, white cabbage, savoy cabbage and kohlrabi. The most preferred crops are broccoli and cauliflower.

The present invention is directed to the species within *Brassica oleracea* that are affected by infection with *Hyaloperonospora brassicae.*

QTL mapping studies were performed on an internal population to identify the genetic regions responsible for the trait of the invention, namely resistance to *Hyaloperonospora brassicae.* On all generations bio-assays were carried out to confirm and monitor the resistance in the various populations, and to determine the inheritance. The identification of a QTL gives the opportunity to use linked markers to identify the presence of the resistance, which is obviously much more efficient than the use of a bio-assay.

For this purpose a first QTL mapping on F2 populations identified a QTL region located on chromosome 8, a QTL region located on chromosome 4, and a QTL region located on chromosome 1. The QTLs were confirmed by a mapping in a F3 population. The QTL mapping was performed with three different *Hyaloperonospora brassicae* isolates.

Resistance to *Hyaloperonospora brassicae* of the present invention is caused by a QTL on chromosome 8 optionally in combination with a QTL on chromosome 4 and/or a QTL on chromosome 1, which are inherited in a semi-dominant manner. This means that a higher resistance level against *Hyaloperonospora brassicae* is achieved when the QTL on chromosome 8, the QTL on chromosome 4 and the QTL on chromosome 1 are present homozygously as compared to a plant which may comprise the QTL on chromosome 8, the QTL on chromosome 4 and the QTL on chromosome 1 heterozygously. Therefore, the heterozygous presence of the QTL on chromosome 8, the QTL on chromosome 4 and the QTL on chromosome 1 in the genome of a plant does confer resistance against *Hyaloperonospora brassicae*, which is between the resistance phenotype of a plant that does not comprise the QTL located on chromosome 8, the QTL on chromosome 4 and the QTL on chromosome 1 and a plant that may comprise the QTL on chromosome 8, the QTL on chromosome 4 and the QTL on chromosome 1 homozygously.

The invention relates to a *Brassica* plant, in particular a *Brassica oleracea* plant, that is resistant to *Hyaloperonospora brassicae*, which may comprise a QTL on chromosome 8 which confers resistance to *Hyaloperonospora brassicae* to the *Brassica* plant.

The invention further relates to a *Brassica* plant, that is resistant to *Hyaloperonospora brassicae*, which may comprise a QTL on chromosome 8 which confers resistance to *Hyaloperonospora brassicae* to the *Brassica* plant, and wherein the resistance is detectable in the cotyledon stage. The resistance is preferably detected by using the bio-assay described in Example 1.

To test whether a *Brassica* plant is resistant to *Hyaloperonospora brassicae*, a bio-assay on the cotyledons is performed. About 20 seeds per plots are sown and one row between two plots is left empty. *Brassica* plants are grown under standard Dutch greenhouse conditions at a temperature regime of 15° C./15° C. night/day. At 10 days after sowing the cotyledons are sprayed with the sporangial suspension of "isolate 2". The inoculated cotyledons are incubated under controlled conditions being a 12° C./14° C. night/day regime. Each plant is visually scored according to Table 1 at 7 days and 14 days after inoculation to phenotypically identify *Hyaloperonospora brassicae* resistant *Brassica* plants. Plants of the invention show resistance after 7 and 14 days after inoculation i.e. the average score of the plants is 1 to 7 when scored according to Table 1. The invention further relates to a *Brassica* plant that is resistant to *Hyaloperonospora brassicae*, which may comprise the QTL of the invention on chromosome 8 and the QTL of the invention on chromosome 4, which shows increased *Hyaloperonospora brassicae* resistance, when the two QTLs are homozygously present, as compared to the resistance when only the QTL of the invention on chromosome 8 is present. The invention further relates to a *Brassica* plant which may comprise the QTL of the invention on chromosome 8 and the QTL of the invention on chromosome 1, which shows increased of *Hyaloperonospora brassicae* resistance, when the two QTLs are homozygously present, as compared to the resistance when only the QTL of the invention on chromosome 8 is present.

The QTL of the invention on chromosome 8 is located between SEQ ID NOS: 1 and 7. In one embodiment, the QTL on chromosome 8 is located between SEQ ID NOS: 2 and 6.

The QTL of the invention on chromosome 4 is located between SEQ ID NOS: 8 and 16. In one embodiment the QTL of the invention on chromosome 4 is located between SEQ ID NOS: 9 and 16.

The QTL of the invention on chromosome 1 is located between SEQ ID NOS: 17 and 22, preferably the QTL of the invention on chromosome 1 is located between SEQ ID NOS: 17 and 21. SEQ ID NOS: 1 and 7 are suitable for identifying the presence of the QTL on chromosome 8. SEQ ID NOS: 8 and 16 are suitable for identifying the presence of the QTL on chromosome 4. SEQ ID NOS: 17 and 22 are suitable for identifying the presence of the QTL on chromosome 1. A further marker suitable for identifying the presence of the QTL on chromosome 8 is selected from the group consisting of SEQ ID NOS: 2 to 6, or any other polymorphism between susceptible and resistant plants that is located between SEQ ID NO: 1 and SEQ ID NO: 7. A further marker suitable for identifying the presence of the QTL on chromosome 4 is selected from the group consisting of SEQ ID NOS: 9 to 15, or any other polymorphism between susceptible and resistant plants that is located between SEQ ID NO: 8 and SEQ ID NO: 16. A further marker suitable for identifying the presence of the QTL on chromosome 1 is selected from the group consisting of SEQ ID NOS: 18 to 21, or any other polymorphism between susceptible and resistant plants that is located between SEQ ID NO: 17 and SEQ NO: 22 or that is located between SEQ ID NO: 17 and SEQ ID NO: 21. These markers can further be used to identify the presence of a QTL for *Hyaloperonospora brassicae* resistance on chromosome 8, 4, or 1 in any other population that may comprise said QTL.

Preferably, one or more markers for identifying the presence of the QTL on chromosome 8 are selected from the group consisting of SEQ ID NOS: 2, 4 and 6. Alternatively, one or more markers for identifying the presence of the QTL on chromosome 8 are selected from the group consisting of SEQ ID NOS: 1, 4, 5 and 7. Alternatively, one or more markers for identifying the presence of the QTL on chromosome 8 are selected from the group consisting of SEQ ID NOS:1, 3, 4, 5, 6 and 7 or from the group consisting of SEQ ID NOS: 1, 2, 3, 4 and 5.

Preferably, one or more markers for identifying the presence of the QTL on chromosome 4 are selected from the group consisting of SEQ ID NOS: 10, 11, 13, 14 and 16. Alternatively, one or more markers for identifying the presence of the QTL on chromosome 4 are selected from the group consisting of SEQ ID NOS: 9, 10, 12 and 15. Alternatively, one or more markers for identifying the presence of the QTL on chromosome 4 are selected from the group consisting of SEQ ID NOS: 8, 12 and 15. Alternatively, one or more markers for identifying the presence of the QTL on chromosome 4 are selected from the group consisting of SEQ ID NOS: 9, 12 and 15. Preferably, one or more markers for identifying the presence of the QTL on chromosome 1 are selected from the group consisting of SEQ ID NOS: 17, 20, 21 and 22. Alternatively, one or more markers for identifying the presence of the QTL on chromosome 1 are selected from the group consisting of SEQ ID NOS: 18, 20 and 21. Alternatively, one or more markers for identifying the presence of the QTL on chromosome 1 are selected from the group consisting of SEQ ID NOS: 17, 18 and 20. Alternatively, one or more markers for identifying the presence of the QTL on chromosome 1 are selected from the group consisting of SEQ ID NOS: 17, 19, 21 and 22. Alternatively, one or more markers for identifying the presence of the QTL on chromosome 1 are selected from the group consisting of SEQ ID NOS: 17, 19 and 22.

The invention relates to a *Brassica* plant showing resistance to *Hyaloperonospora brassicae* and which may comprise at least one marker selected from the group consisting of SEQ ID NOS: 1 to 7, preferably selected from the group consisting of SEQ ID NOS: 2, 4 and 6, in its genome, which is linked to said resistance. Alternatively, the *Brassica* plant showing resistance to *Hyaloperonospora brassicae* and may comprise at least one marker selected from the group consisting of SEQ ID NOS: 1, 4, 5 and 7, or selected from the group consisting of SEQ ID NOS: 1, 2, 4 and 5, from the group consisting of SEQ ID NOS: 1, 3, 4, 5, 6 and 7, or selected from the group consisting of SEQ ID NOS: 1, 2, 3, 4 and 5. The invention also relates to a *Brassica* plant showing resistance to *Hyaloperonospora brassicae* and which may comprise at least one marker selected from the group consisting of SEQ ID NOS: 8 to 16, preferably selected from the group consisting of SEQ ID NOS: 10, 11, 13, 14 and 16, or selected from the group consisting of SEQ ID NOS: 9, 10, 12 and 15, or selected from the group consisting of SEQ ID NOS: 8, 12 and 15, or selected from the group consisting of SEQ ID NOS: 9, 12 and 15, which is linked to said resistance when present in a plant with the QTL of the invention on chromosome 8, and/or at least one marker selected from the group consisting of SEQ ID NOS: 17 to 22, preferably selected from the group consisting of SEQ ID NOS: 17, 20, 21 and 22, or selected from the group consisting of SEQ ID NOS: 18, 20 and 21, or selected from the group consisting of SEQ ID NOS: 17, 18 and 20, or selected from the group consisting of SEQ ID NOS: 17, 19, 21 and 22, or selected from the group consisting of SEQ ID NOS: 17, 19 and 22, which is linked to said resistance when present in a plant with the QTL of the invention on chromosome 8, FIG. 1 gives the sequences of the SEQ ID NOS: that can be used as markers, or used to develop markers, to identify the presence of a QTL leading to *Hyaloperonospora brassicae* resistance in a *Brassica* plant. Table 3 shows the marker score that identifies the presence of the QM, and therefore a plant showing resistance to *Hyaloperonospora brassicae*, as well as the position of the SNP in the sequence of FIG. 1. When the sequences of the markers are positioned on for example version V1.0 of the publicly available genome reference sequence for *Brassica oleracea*, the physical position to which the SNP polymorphism in said marker sequence corresponds can be derived. Version V1.0 of the public *Brassica oleracea* genome reference sequence can for example be accessed at the *Brassica* Database website (brassicadb.org) and is the reference for 'the public *Brassica oleracea* genome' as used herein. The positions of the QTLs and the markers of the invention are derivable from a public map and these positions are relative to said physical positions, Identifying the presence of a marker is in particular done by identifying the presence of the nucleotide at the position of the SNP that is indicative for the resistance, as present in any of the sequences determining the SEQ ID Nos, as compared to the wild type nucleotide at the position of the SNP; the locations and nucleotide of the SNPs that are indicative for resistance are indicated in Table 3.

A *Brassica* plant that may comprise the QTL of the invention on chromosome 8, the QTL of the invention on chromosome 4 and the QTL of the invention on chromosome 1, all homozygously, can be grown from seed as deposited with the NCIMB under accession number NCIMB 43346.

The seed deposited with the NCIMB under accession number NCIMB 43346 has the *Hyaloperonospora brassicae* resistance as described herein and may comprise a QTL on chromosome 8 that can be identified by determining the presence of at least one of the markers of the group consisting of SEQ ID NOS: 1 to 7, preferably selected from the group consisting of SEQ ID NOS: 2, 4 and 6. Alternatively, one or more markers for identifying the presence of the QTL on chromosome 8 are selected from the group consisting of SEQ ID NOS: 1, 4, 5 and 7. Alternatively, one or more markers for identifying the presence of the QTL on chromosome 8 are selected from the group consisting of SEQ ID NOS:1, 3, 4, 5, 6 and 7 or from the group consisting of SEQ ID NOS:1, 2, 3, 4 and 5, a QTL on chromosome 4 that can be identified by determining the presence of at least one of the markers of the group consisting of SEQ ID NOS: 8 to 16, preferably selected from the group consisting of SEQ ID NOS: 10, 11, 13, 14 and 16. Alternatively, one or more markers for identifying the presence of the QTL on chromosome 4 are selected from the group consisting of SEQ ID NOS: 9, 10, 12 and 15. Alternatively, one or more markers for identifying the presence of the QTL on chromosome 4 are selected from the group consisting of SEQ ID NOS: 8, 12 and 15. Alternatively, one or more markers for identifying the presence of the QTL on chromosome 4 are selected from the group consisting of SEQ ID NOS: 9, 12 and 15. Preferably, one or more markers for identifying the presence of the QTL on chromosome 1 are selected from the group consisting of SEQ ID NOS:17, 20, 21 and 22, and a QTL on chromosome 1 that can be identified by determining the presence of at least one of the markers of the group consisting of SEQ ID NOS: 17 to 22, preferably selected from the group consisting of SEQ ID NOS: 18, 20 and 21. Alternatively, one or more markers for identifying the presence of the QTL on chromosome 1 are selected from the group consisting of SEQ ID NOS: 17, 18 and 20. Alternatively, one or more markers for identifying the presence of the QTL on chromosome 1 are selected from the group consisting of SEQ ID NOS: 17, 19, 21 and 22. Alternatively, one or more markers for identifying the presence of the QTL on chromosome 1 are selected from the group consisting of SEQ ID NOS: 17, 19 and 22.

A plant which may comprise the QTL of the invention on chromosome 8, the QTL of the invention on chromosome 4, and the QTL of the invention on chromosome 1, preferably all homozygously, can be used as a resistant control variety in a *Hyaloperonospora brassicae* bio-assay. When a plant, line, or population to be assessed shows the same level of resistance as a plant grown from the seed deposited with the NCIMB under accession number NCIMB 43346, and this plant, line or population may comprise the QTL of the invention on chromosome 8, the QTL of the invention on chromosome 4, and the QTL of the invention on chromosome 1, this plant, line, or population is considered to have the *Hyaloperonospora brassicae* resistance of the invention and is therefore a plant of the invention.

The present invention provides a QTL on chromosome 8, which QTL is linked to at least one of the markers which may comprise any of the SEQ ID NOS: 1 to 7, and preferably at least the marker which may comprise SEQ ID NO: 4, wherein the presence of said QTL in a *Brassica* plant leads to *Hyaloperonospora brassicae* resistance.

The present invention provides a QTL on chromosome 4, which QTL is linked to at least one of the markers which may comprise any of the SEQ ID NOS: 8 to 16, and preferably at least the markers which may comprise SEQ ID NO: 10 and or SEQ ID NO:11, and more preferably at least the markers which may comprise SEQ ID NO: 10, wherein the presence of said QTL in combination with the QTL of the invention on chromosome 8, both homozygously present in a *Brassica* plant leads to an increased resistance to *Hyaloperonospora brassicae*, as compared to the resistance when only the QTL of the invention on chromosome 8 is present.

The present invention provides a QTL on chromosome 1, which QTL is linked to at least one of the markers which may comprise any of the SEQ ID NOS: 17 to 22, and preferably at least the marker which may comprise SEQ ID NO: 20 or the marker which may comprise SEQ ID NO: 18, wherein the presence of said QTL in combination with the QTL of the invention on chromosome 8, both homozygously present in a *Brassica* plant leads to an increased *Hyaloperonospora brassicae* resistance, as compared to the resistance when only the QTL of the invention on chromosome 8 is present.

The invention relates to a *Brassica* plant which may comprise the QTL of the invention on chromosome 8 and the QTL of the invention on chromosome 4 or the QTL of the invention on chromosome 1, both QTLs homozygously present, wherein said plant has an increased resistance to *Hyaloperonospora brassicae* as compared to the *Hyaloperonospora brassicae* resistance of a *Brassica* plant which may comprise only the QTL on chromosome 8.

The invention further relates to a *Brassica* plant which may comprise the QTL of the invention on chromosome 8 homozygously and the QTL of the invention on chromosome 4 homozygously and the QTL of the invention on chromosome 1 heterozygously, wherein said plant has an increased resistance to *Hyaloperonospora brassicae* as compared to the *Hyaloperonospora brassicae* resistance of a *Brassica* plant which may comprise only the QTL of the invention on chromosome 8 and the QTL of the invention on chromosome 4 or the QTL of the invention on chromosome 1.

The invention further relates to a *Brassica* plant which may comprise the QTL of the invention on chromosome 8 homozygously and the QTL of the invention on chromosome 4 heterozygously and the QTL of the invention on chromosome 1 homozygously, wherein said plant has an increased resistance to *Hyaloperonospora brassicae* as compared to the *Hyaloperonospora brassicae* resistance of a *Brassica* plant which may comprise only the QTL of the invention on chromosome 8 and the QTL of the invention on chromosome 4 or the QTL of the invention on chromosome 1.

The invention further relates to a *Brassica* plant which may comprise the QTL of the invention on chromosome 8 and the QTL of the invention on chromosome 4 and the QTL of the invention on chromosome 1, all three QTLs homozygously, wherein said plant has an increased resistance to *Hyaloperonospora brassicae* as compared to the *Hyaloperonospora brassicae* resistance of a *Brassica* plant which may comprise only the QTL of the invention on chromosome 8 and the QTL of the invention on chromosome 4 or the QTL of the invention on chromosome 1.

The invention also relates to a method for producing a *Brassica* plant that is resistant to *Hyaloperonospora brassicae*, which may comprise introducing the QTL of the invention on chromosome 8 and optionally the QTL of the invention on chromosome 4 and/or the QTL of the invention on chromosome 1 into a *Brassica* plant.

A QTL of the invention can be introduced into a plant from another plant which may comprise the QTL through commonly used breeding techniques, such as crossing and selection, when the plants are sexually compatible. Such introduction can be from a plant of the same species, that usually can be crossed easily, or from a plant of a related species. Difficulties in crossing can be overcome through techniques known in the art such as embryo rescue, or cisgenesis can be applied. A QTL of the invention can also be introduced by other means, such as mutagenesis or genetic modification. Suitably markers as described herein are used to follow the incorporation of the QTL into another plant.

The present invention relates to a method for producing a *Brassica* plant which is resistant to *Hyaloperonospora brassicae*, said method which may comprise:
 a) crossing a *Brassica* plant of the invention with another plant to obtain an F1 population;
 b) optionally performing one or more rounds of selfing and/or crossing a plant from the F1 to obtain a further generation population;
 c) selecting from the further generation population a plant that may comprise the QTL on chromosome 8, and optionally the QTL on chromosome 4 and/or the QTL on chromosome 1, and which is resistant to *Hyaloperonospora brassicae*.

The plant of the invention used in the method for the production of a *Brassica* plant which is resistant against *Hyaloperonospora brassicae* may be a plant grown from seed deposited with the NCIMB under accession number NCIMB 43346, or a progeny plant thereof that has obtained a QTL of the invention causing resistance against *Hyaloperonospora brassicae* therefrom.

The invention further relates to a method for producing a *Brassica* plant which is resistant to *Hyaloperonospora brassicae* as described herein, wherein the selection of a plant which may comprise the QTL on chromosome 8, and optionally the QTL on chromosome 4 and/or the QTL on chromosome 1, is suitably done by using a molecular marker selected from the group consisting of SEQ ID NOS: 1 to 7, preferably from the group consisting of SEQ ID NOS: 2, 4 and 6. Alternatively, one or more markers for identifying the presence of the QTL on chromosome 8 are selected from the group consisting of SEQ ID NOS: 1, 4, 5 and 7. Alternatively, one or more markers for identifying the presence of the QTL on chromosome 8 are selected from the group consisting of SEQ ID NOS:1, 3, 4, 5, 6 and 7 or from the group consisting of SEQ ID NOS:1, 2, 3, 4 and 5 for the identification of the QTL on chromosome 8; or from the group consisting of SEQ ID NOS: 8 to 16, preferably from the group consisting of SEQ ID NOS: 10, 11, 13, 14 and 16. Alternatively, one or more markers for identifying the presence of the QTL on chromosome 4 are selected from the group consisting of SEQ ID NOS: 9, 10, 12 and 15. Alternatively, one or more markers for identifying the presence of the QTL on chromosome 4 are selected from the group consisting of SEQ ID NOS: 8, 12 and 15. Alternatively, one or more markers for identifying the presence of the QTL on chromosome 4 are selected from the group consisting of SEQ ID NOS: 9, 12 and 15 for the identification of the QTL on chromosome 4, or from the group consisting of SEQ ID NOS: 17 to 22, preferably from the group consisting; of SEQ ID NOS: 17, 20, 21 and 22. Alternatively, one or more markers for identifying the presence of the QTL on chromosome 1 are selected from the group consisting of SEQ ID NOS: 18, 20 and 21. Alternatively, one or more markers for identifying the presence of the QTL on chromosome 1 are selected from the group consisting of SEQ ID NOS: 17, 18 and 20. Alternatively, one or more markers for identifying the presence of the QTL on chromosome 1 are selected from the group consisting of SEQ ID NOS: 17, 19, 21 and 22. Alternatively, one or more markers for identifying the presence of the QTL on chromosome 1 are selected from the group consisting of SEQ H) NOS: 17, 19 and 22 for the identification of the QTL on chromosome 1.

The invention additionally provides for a method of introducing another desired trait into a *Brassica* plant resistant to *Hyaloperonospora brassicae*, which may comprise:
 a) crossing a *Brassica* plant of the invention with a second *Brassica* plant that may comprise the other desired trait to produce F1 progeny;
 b) optionally selecting in the F1 for a plant that shows resistance to *Hyaloperonospora brassicae* and the other desired trait;
 c) crossing the optionally selected F1 progeny with either parent, to produce backcross progeny;
 d) selecting backcross progeny shows resistance to *Hyaloperonospora brassicae* and the other desired trait; and
 e) optionally repeating steps c) and d) one or more times in succession to produce selected fourth or higher backcross progeny that may comprise the other desired trait and shows resistance to *Hyaloperonospora brassicae*.

The plant of the invention used in the method of introducing another desired trait into a *Brassica* plant showing resistance to *Hyaloperonospora brassicae* may be a plant grown from seed deposited with the NCIMB under accession number NCIMB 43346, or a progeny plant thereof that has obtained a QTL of the invention causing resistance against *Hyaloperonospora brassicae* therefrom.

The above method can in particular be used to introduce a QTL of the invention into a plant species that is suitable for incorporation of such genetic information. In particular, said QTL can be introduced from a *Brassica oleracea* plant which may comprise the QTL into a *Brassica oleracea* plant lacking the QTL, for example by using standard breeding methods.

The QTL of the invention on chromosome 8, and optionally the QTL of the invention on chromosome 4 and/or the QTL of the invention on chromosome 1, can be introduced from a *Brassica oleracea* plant representative seed of which was deposited with the NCIMB under accession number NCIMB 43346, or from sexual or vegetative descendants thereof. Introduction of the QTL of the invention on chromosome 8, and optionally the QTL of the invention on chromosome 4 and/or the QTL of the invention on chromosome 1 in *Brassica oleracea* leads to resistance to *Hyaloperonospora brassicae*.

Optionally, selfing steps are performed after any of the crossing or backcrossing steps. Selection of a plant showing resistance to *Hyaloperonospora brassicae* and the other desired trait can alternatively be done following any crossing or selfing step of the method. The other desired trait can be selected from, but is not limited to, the following group: resistance to bacterial, fungal or viral diseases, insect or pest resistance, improved germination, plant size, plant type, improved shelf-life, water stress and heat stress tolerance, and male sterility. The invention includes a *Brassica* plant produced by this method and a *Brassica* part obtained therefrom.

The invention further relates to the use of a *Brassica* plant of the invention for transferring the resistance to *Hyaloperonospora brassicae* into another *Brassica* plant.

The invention also relates to the use of seeds that were deposited with the NCIMB under accession number NCIMB 43346 on Feb. 4, 2019, for transferring the resistance to *Hyaloperonospora brassicae* into another *Brassica* plant.

The invention further relates to a method for the production of a *Brassica* plant which may comprise the QTL of the invention on chromosome 8 and optionally the QTL of the invention on chromosome 4 and/or the QTL of the invention on chromosome 1, wherein the presence of said QTL or combination of QTLs leads to resistance to *Hyaloperonospora brassicae*, by using tissue culture of plant material that may comprise the QTL or combination of QTLs of the invention in its genome.

The invention further relates to a method for the production of a *Brassica* plant which may comprise the QTL of the invention on chromosome 8 and optionally the QTL of the invention on chromosome 4 and/or the QTL of the invention on chromosome 1, which QTL or combination of QTLs confers resistance to *Hyaloperonospora brassicae*, by using vegetative reproduction of plant material that may comprise the QTL or combination of QTLs of the invention in its genome.

The invention further provides a method for the production of a *Brassica* plant having resistance to *Hyaloperonospora brassicae* as defined herein by using a doubled haploid generation technique to generate a doubled haploid line that homozygously may comprise a QTL or combination of QTLs of the invention and shows resistance against *Hyaloperonospora brassicae*.

The invention further relates to *Brassica* plants of the invention that have acquired the QTL of the invention on chromosome 8, and optionally the QTL of the invention on chromosome 4 and/or the QTL of the invention on chromosome 1 from a suitable source, either by conventional breeding, or genetic modification, in particular by cisgenesis or transgenesis. Cisgenesis is a genetic modification of plants with a natural gene, encoding a (agricultural) trait from the crop plant itself or from a sexually compatible donor plant. Transgenesis is a genetic modification of a plant with a gene from a non-crossable species or with a synthetic gene.

Alternatively a QTL of the invention can be transferred from another, sexually incompatible, plant, for example by using a transgenic approach. Techniques that can suitably be used comprise general plant transformation techniques known to the skilled person, such as the use of an *Agrobacterium*-mediated transformation method. Genome editing methods such as the use of a CRISPR/Cas system might also be employed to obtain a plant of the invention.

The invention relates to a method for production of a plant showing resistance to *Hyaloperonospora brassicae* which may comprise the steps of:
a) introducing a mutation in a population of *Brassica* plants;
b) selecting a *Brassica* plant showing resistance to *Hyaloperonospora brassicae;*
c) assaying genomic nucleic acids of the plant selected under b) for the presence of a genomic *Hyaloperonospora brassicae* resistance marker genetically linked the QTL of the invention on chromosome 8, and optionally the QTL of the invention on chromosome 4 and/or the QTL of the invention on chromosome 1, which confer the resistance to *Hyaloperonospora brassicae* to the *Brassica* plant, said *Hyaloperonospora brassicae* resistance marker being within at least 30 cM, 20 cM, 15 cM, 10 cM, 5 cM or 1 cM of any of the SEQ ID Nos: 1 to 22; and
d) growing or cultivating the *Brassica* plant obtained under c).

A plant of the invention which may comprise the QTL of the invention on chromosome 8, and optionally the QTL of the invention on chromosome 4 and/or the QTL of the invention on chromosome 1, may be a plant of an inbred line, a hybrid, a doubled haploid, or a plant of a segregating population. Preferably, the plant of the invention is a non-transgenic plant.

The invention further relates to a *Brassica* seed which may comprise the QTL of the invention on chromosome 8 and optionally the QTL of the invention on chromosome 4 and/or the QTL of the invention on chromosome 1, wherein the plant grown from the seed is a plant of the invention that shows resistance to *Hyaloperonospora brassicae*. The invention also relates to seed produced by a plant of the invention. This seed harbors the QTL of the invention on chromosome 8 and optionally the QTL of the invention on chromosome 4 and/or the QTL of the invention on chromosome land as such, a plant grown from said seed is a plant of the invention.

The invention also relates to harvested parts of *Brassica* plants of the invention or parts thereof, to food products which may comprise harvested parts of *Brassica* plants of the invention or parts thereof, either in natural or optionally in processed form. The harvested part or food product can be or may comprise a cabbage head, a curd, a stem, a leaf, a root, a sprout, a seed, or any other part of a *Brassica* plant. The harvested part may also be used for the production of bio-fuel. The food product or harvested part may have undergone one or more processing steps. Such a processing step might comprise but is not limited to any one of the following treatments or combinations thereof: cutting, washing, cooking, steaming, baking, frying, pasteurizing, freezing, grinding, extracting oil, pickling, or fermenting. The processed form that is obtained is also part of this invention.

The invention also relates to propagation material suitable for producing a *Brassica* plant of the invention, wherein the propagation material is suitable for sexual reproduction, and is in particular selected from a microspore, pollen, an ovary, an ovule, an embryo sac, and an egg cell; or is suitable for vegetative reproduction, and is in particular selected from a cutting, a root, a stem, a cell, a protoplast, and tissue cultures of the *Brassica* plant of the invention. The tissue culture may comprise regenerable cells, such a tissue culture can be derived from a leaf, pollen, embryo, cotyledon, hypocotyl, meristematic cell, root tip, anther, flower, seed or stem. The propagation material may comprise the QTL of the invention on chromosome 8 and optionally the QTL of the invention on chromosome 4 and/or the QTL of the invention on chromosome 1 that causes the resistance to *Hyaloperonospora brassicae* of the invention.

The invention further relates to a *Brassica* plant grown or regenerated from the said propagation material of a plant of the invention, which *Brassica* plant shows resistance to *Hyaloperonospora brassicae*.

The invention further relates to a tissue culture of a *Brassica* plant showing resistance to *Hyaloperonospora*, that can be regenerated into a *Brassica* plant with resistance to *Hyaloperonospora brassicae*, which tissue culture may comprise the QTL of the invention on chromosome 8 and optionally the QTL of the invention on chromosome 4 and/or the QTL of the invention on chromosome 1.

The invention further relates to a cell of a *Brassica* plant showing resistance to *Hyaloperonospora brassicae* which may comprise the QTL of the invention on chromosome 8 and optionally the QTL of the invention on chromosome 4 and/or the QTL of the invention on chromosome 1. A cell of the invention can be obtained from, or be present in, a plant of the invention. Such a cell may either be in isolated form, or a part of a complete plant, or from a part thereof, and still constitutes a cell of the invention because such a cell may comprise the genetic information that determines a QTL as described herein that leads to resistance to *Hyaloperonospora brass/ale* of a cultivated *Brassica* plant. Each cell of a plant of the invention carries the genetic information that leads to resistance to *Hyaloperonospora brassicae*. A cell of the invention may also be a regenerable cell that can regenerate into a new plant of the invention. The presence of the genetic information in this context is the presence of the QTL, of the invention on chromosome 8 and optionally the QTL of the invention on chromosome 4 and/or the QTL of the invention on chromosome 1.

The invention further relates to a tissue culture of regenerable cells or protoplasts obtained from the *Brassica* plant of the invention, wherein the tissue culture can be derived from a leave, pollen, embryo, cotyledon, hypocotyl, meristematic cell, root tip, anther, flower, seed or stem.

The invention moreover relates to progeny of a plant, a cell, a tissue, or a seed of the invention, which progeny may comprise the QTL of the invention on chromosome 8 and optionally the QTL of the invention on chromosome 4 and/or the QTL of the invention on chromosome 1. Such progeny can in itself be a plant, a cutting, a seed, a cell, or a tissue. The progeny of the plant, cell, tissue, or seed of the invention is resistant to *Hyaloperonospora brassicae* due to the presence therein of the QTL of the invention on chromosome 8, and optionally the QTL of the invention on chromosome 4 and/or the QTL of the invention on chromosome 1.

The invention further relates to the germplasm of plants of the invention. The germplasm is constituted by all inherited characteristics of an organism and according to the invention encompasses at least the trait of the invention. The germplasm can be used in a breeding program for the development of cultivated *Brassica* plants having resistance to *Hyaloperonospora brassicae*. The use of germplasm that may comprise the QTL of the invention on chromosome 8, and optionally the QTL of the invention on chromosome 4 and/or the QTL of the invention on chromosome 1, which confer resistance to *Hyaloperonospora brassicae* in breeding is also part of the present invention.

The invention additionally relates to the use of a plant of the invention in plant breeding. The invention thus also relates to a breeding method for the development of a cultivated *Brassica* plant that has resistance to *Hyaloperonospora brassicae*, wherein a plant which may comprise the QTL of the invention on chromosome 8 and optionally the QTL of the invention on chromosome 4 and/or the QTL of the invention on chromosome 1, for conferring said resistance to another plant is used. Seed being representative for a plant that can be used in plant breeding to develop another plant with resistance to *Hyaloperonospora brassicae* was deposited with the NCIMB under accession number NCIMB 43346.

The invention also concerns the use of the QTL of the invention on chromosome 8 and optionally the QTL of the invention on chromosome 4 and/or the QTL of the invention on chromosome 1, for the development of *Brassica* plants that have resistance to *Hyaloperonospora brassicae*.

The invention also relates to markers for the identification of the QTL on chromosome 8, the QTL on chromosome 4 and the QTL on chromosome 1, which QTLs when present in the genome of a *Brassica* plant confers resistance to *Hyaloperonospora brassicae*, wherein the marker is selected from the group consisting of SEQ ID NOS: 1 to 22, or any combination thereof.

The invention also relates to a marker for the identification of the QTLs, which when present in a plant confer *Hyaloperonospora brassicae* resistance, and which marker is selected from the group consisting of SEQ ID NOS: 1 to 7, preferably from the group consisting of SEQ ID NOS: 2, 4 and 6. Alternatively, one or more markers for identifying the presence of the QTL on chromosome 8 are selected from the group consisting of SEQ ID NOS: 1, 4, 5 and 7. Alternatively, one or more markers for identifying the presence of the QTL on chromosome 8 are selected from the group consisting of SEQ ID NOS:1, 3, 4, 5, 6 and 7 or from the group consisting of SEQ ID NOS:1, 2, 3, 4 and 5 for the identification of the QTL on chromosome 8; or from the group consisting of SEQ ID NOS: 8 to 16, preferably from the group consisting of SEQ ID NOS: 10, 11, 13, 14 and 16. Alternatively, one or more markers for identifying the presence of the QTL on chromosome 4 are selected from the group consisting of SEQ ID NOS: 9, 10, 12 and 15. Alternatively, one or more markers for identifying the presence of the QTL on chromosome 4 are selected from the group consisting of SEQ ID NOS: 8, 12 and 15. Alternatively, one or more markers for identifying the presence of the QTL on chromosome 4 are selected from the group consisting of SEQ ID NOS: 9, 12 and 15 for the identification of the QTL on chromosome 4, or from the group consisting of SEQ ID NOS: 17 to 22, preferably from the group consisting of SEQ ID NOS: 17, 20, 21 and 22. Alternatively, one or more markers for identifying the presence of the QTL on chromosome 1 are selected from the group consisting of SEQ ID NOS: 18, 20 and 21. Alternatively, one or more markers for identifying the presence of the QTL on chromosome 1 are selected from the group consisting of SEQ ID NOS: 17, 18 and 20. Alternatively, one or more markers for identifying the presence of the QTL on chromosome 1 are selected from the group consisting of SEQ ID NOS: 17, 19, 21 and 22. Alternatively, one or more markers for identifying the presence of the QTL on chromosome 1 are selected from the group consisting of SEQ ID NOS: 17, 19 and 22 for the identification of the QTL on chromosome 1. The use of any of the markers which may comprise SEQ ID NOS: 1 to 22 for identification of *Hyaloperonospora brassicae* resistance as described herein, in a *Brassica* plant is also part of the invention. Any of these markers can also be used to develop other markers for the identification of a QTL which confers resistance to *Hyaloperonospora brassicae* when present in a plant, which use of said marker is also part of the present invention.

The invention relates to a method for selecting a *Brassica* plant or *Brassica* seed for resistance to *Hyaloperonospora brassicae* which may comprise:
  a) assaying genomic nucleic acids of *Brassica* plant or *Brassica* seed for the presence of a genomic *Hyaloperonospora brassicae* resistance marker genetically linked to the QTL of the invention on chromosome 8, and optionally the QTL of the invention on chromosome 4 and/or the QTL of the invention on chromosome 1, the resistance to *Hyaloperonospora brassicae* to the *Brassica* plant, said genomic *Hyaloperonospora brassicae* resistance marker being at least within at least 30 cM, 20 cM, 15 cM, 10 cM, 5 cM or 1 cM of any of SEQ ID NOS: 1 to 22;
  b) determining whether said genomic *Hyaloperonospora brassicae* resistance marker is homozygous or heterozygous; and
  c) selecting said *Brassica* plant or *Brassica* seed based on said determination.

The present invention also relates to a method for selecting a *Brassica* plant showing resistance to *Hyaloperonospora brassicae*, which may comprise identifying the presence of the QTL of the invention on chromosome 8 and optionally the QTL of the invention on chromosome 4 and/or the QTL of the invention on chromosome 1, and selecting a plant that may comprise said QTL(s) as a *Brassica* plant with resistance to *Hyaloperonospora brassicae*. Identifying the presence of the QTL on chromosome 8 is suitably done using a marker selected from the group consisting of SEQ ID NOS: 1 to 7, preferably from the group consisting of SEQ ID NOS: 2, 4 and 6. Alternatively, one or more markers for identifying the presence of the QTL on chromosome 8 are selected from the group consisting of SEQ ID NOS: 1, 4, 5 and 7. Alternatively, one or more markers for identifying the presence of the QTL on chromosome 8 are selected from the group consisting of SEQ ID NOS:1, 3, 4, 5, 6 and 7 or from the group consisting of SEQ ID NOS:1, 2, 3, 4 and 5. Identifying the presence of the QTL on chromosome 4 is suitably done using a marker selected from the group consisting of SEQ ID NOS: 8 to 16, preferably from the group consisting of SEQ ID NOS: 10, 11, 13, 14 and 16. Alternatively, one or more markers for identifying the presence of the QTL on chromosome 4 are selected from the group consisting of SEQ ID NOS: 9, 10, 12 and 15. Alternatively, one or more markers for identifying the presence of the QTL on chromosome 4 are selected from the group consisting of SEQ ID NOS: 8, 12 and 15. Alternatively, one or more markers for identifying the presence of the QTL on chromosome 4 are selected from the group consisting of SEQ ID NOS: 9, 12 and 15. Identifying the presence of the QTL on chromosome 1 is suitably done using a marker selected from the group consisting of SEQ ID NOS: 17 to 22, preferably from the group consisting of SEQ ID NOS: 17, 20, 21 and 22. Alternatively, one or more markers for identifying the presence of the QTL on chromosome 1 are selected from the group consisting of SEQ ID NOS: 18, 20 and 21. Alternatively, one or more markers for identifying the presence of the QTL on chromosome 1 are selected from the group consisting of SEQ ID NOS: 17, 18 and 20. Alternatively, one or more markers for identifying the presence of the QTL on chromosome 1 are selected from the group consisting of SEQ ID NOS: 17, 19, 21 and 22. Alternatively, one or more markers for identifying the presence of the QTL on chromosome 1 are selected from the group consisting of SEQ ID NOS: 17, 19 and 22. The plant can alternatively, or in addition, be phenotypically selected for having resistance to *Hyaloperonospora brassicae*, in particular by performing a bio-assay for *Hyaloperonospora brassicae* resistance.

The invention further relates to a method for selecting a *Brassica* plant or *Brassica* seed for resistance to *Hyaloperonospora brassicae* as described herein, wherein said *Hyaloperonospora brassicae* resistance genomic region can be monitored by assaying for an allele of 1, 2, 3, 4, 5, 6, 7, 10, 11, 12, 13, 14, 15, 16, 17, 18, 19, 20, 21, 22 or more markers of any of SEQ ID Nos: 1 to 22, or complements thereof.

The genomic *Hyaloperonospora brassicae* resistance marker is associated with *Hyaloperonospora brassicae* resistance genomic region located on chromosome 8 identifiable using SEQ ID NOS: 1 to 7, or complements thereof. The *Hyaloperonospora brassicae* resistance marker can be monitored by assaying for an allele of 1, 2, 3, 4, 5, 6, 7, or more markers of SEQ ID No: 1 through SEQ ID No: 7, or complements thereof.

The genomic *Hyaloperonospora brassicae* resistance marker is associated with *Hyaloperonospora brassicae* resistance genomic region located on chromosome 8 identifiable 10 using SEQ ID NOS: 8 to 16, or complements thereof. The *Hyaloperonospora brassicae* resistance marker can be monitored by assaying for an allele of 1, 2, 3, 4, 5, 6, 7, 8, or more markers of SEQ ID No: 8 through SEQ ID No: 16, or complements thereof.

The genomic *Hyaloperonospora brassicae* resistance marker is associated with *Hyaloperonospora brassicae* resistance genomic region located on chromosome 1 identifiable using SEQ ID NOS: 17 to 22, or complements thereof. The *Hyaloperonospora brassicae* resistance marker can be monitored by assaying for an allele of 1, 2, 3, 4, 5, or more markers of SEQ ID No: 17 through SEQ ID No: 22, or complements thereof.

The invention further relates to a method for selecting a *Brassica* plant or *Brassica* seed for resistance to *Hyaloperonospora brassicae* as described herein, further which may comprise obtaining DNA 20 from said *Brassica* plant or seed using a non-destructive method.

The invention also relates to a method for the identification of molecular markers indicative of *Hyaloperonospora brassicae* resistance of a *Brassica* plant, which may comprise:
  a) isolating DNA from said *Brassica* plant and from a susceptible wild type plant;
  b) screening for molecular markers in a region of said DNA sequence corresponding to of any of the SEQ ID Nos: 1 to 22;
  c) determining co-inheritance of said markers from the wild type plant to said plant.

The invention further relates to the molecular marker detectable by this method and to the use of said molecular marker for the selection of a *Brassica* plant that is resistant to *Hyaloperonospora brassicae*.

The invention further relates to the molecular marker and to the use of the molecular marker detected by the method for the identification of molecular markers as described herein.

The invention further relates to a method for seed production which may comprise growing a *Brassica* plant from a seed of the invention, allowing the plant to produce seeds, harvesting the seeds. Production of the seed is suitably done by selfing or by crossing with another plant that is optionally also a plant of the invention. The seed that is so produced has the capability to grow into a plant that shows resistance to *Hyaloperonospora brassicae*.

The invention further relates to hybrid seed and to a method for producing said hybrid seed, which may comprise crossing a first parent plant with a second parent plant and harvesting the resultant hybrid seed, wherein the first parent plant and/or the second parent plant is a plant of the invention which may comprise the QTL of the invention on chromosome 8 and optionally the QTL of the invention on chromosome 4 and/or the QTL of the invention on chromosome 1. The resulting hybrid plant that can be grown from the hybrid seed, which may comprise said QTL or combination of QTLs, which hybrid plant has resistance to *Hyaloperonospora brassicae*, is also a plant of the invention.

It is clear that the parent that provides the trait of the invention is not necessarily a plant grown directly from the deposited seed. The parent can also be a progeny plant from the deposited seed, or a progeny plant from seed that is identified to have obtained the trait of the invention by other means.

The invention relates to the use of a *Brassica* plant which may comprise the QTL of the invention on chromosome 8 and optionally the QTL of the invention on chromosome 4 and/or the QTL of the invention on chromosome 1, which confer resistance to *Hyaloperonospora brassicae*, as a crop. The invention relates to use of a *Brassica* plant which may comprise the QTL of the invention on chromosome 8 and optionally the QTL of the invention on chromosome 4 and/or the QTL of the invention on chromosome 1, which confer resistance to *Hyaloperonospora brassicae*, as a source of seed.

The invention relates to the use of a *Brassica* plant which may comprise the QTL of the invention on chromosome 8 and optionally the QTL of the invention on chromosome 4 and/or the QTL of the invention on chromosome 1, which confer resistance to *Hyaloperonospora brassicae*, as a source of propagating material.

The invention relates to the use of a *Brassica* plant which may comprise the QTL of the invention on chromosome 8 and optionally the QTL of the invention on chromosome 4 and/or the QTL of the invention on chromosome 1, which confer resistance to *Hyaloperonospora brassicae*, for consumption.

The invention relates to use of the QTL of the invention on chromosome 8 and optionally the QTL of the invention on chromosome 4 and/or the QTL of the invention on chromosome 1, which confer resistance to *Hyaloperonospora brassicae*, for conferring resistance to *Hyaloperonospora brassicae* to a *Brassica* plant.

The invention relates to the use of a *Brassica* plant as a recipient of the QTL of the invention on chromosome 8 and optionally the QTL of the invention on chromosome 4 and/or the QTL of the invention on chromosome 1.

As used herein a marker is genetically linked to, and can therefore be used for the identification of, a QTL of the invention, when the marker and the trait co-segregate in a segregating population resulting from a cross between a plant which may comprise a QTL of the invention and a plant lacking the QTL.

As used herein "the QTL of the invention on chromosome 8" is intended to mean the QTL located on chromosome 8 that can be identified by use of at least one of the markers selected from the group consisting of SEQ ID NOS: 1 to 7, preferably from the group consisting of SEQ ID NOS: 2, 4 and 6. Alternatively, one or more markers for identifying the presence of the QTL on chromosome 8 are selected from the group consisting of SEQ ID NOS: 1, 4, 5 and 7. Alternatively, one or more markers for identifying the presence of the QTL on chromosome 8 are selected from the group consisting of SEQ ID NOS:1, 3, 4, 5, 6 and 7 or from the group consisting of SEQ ID NOS:1, 2, 3, 4 and 5, or any other combination of SEQ ID NOS: 1, 2, 3, 4, 5, 6 and 7 and which confers resistance to *Hyaloperonospora brassicae* to a *Brassica* plant, when present in the genome of said *Brassica* plant. As used herein "the QTL of the invention on chromosome 4" is intended to mean the QTL located on chromosome 4 that can be identified by use of at least one of the markers selected from the group consisting of SEQ ID NOS: 8 to 16, preferably from the group consisting of SEQ ID NOS: 10, 11, 13, 14 and 16. Alternatively, one or more markers for identifying the presence of the QTL on chromosome 4 are selected from the group consisting of SEQ ID NOS: 9, 10, 12 and 15. Alternatively, one or more markers for identifying the presence of the QTL on chromosome 4 are selected from the group consisting of SEQ ID NOS: 8, 12 and 15. Alternatively, one or more markers for identifying the presence of the QTL on chromosome 4 are selected from the group consisting of SEQ ID NOS: 9, 12 and 15, or any other combination of SEQ ID NOS: 8, 9, 10, 11, 12, 13, 14, 15 and 16 and which confers increased resistance to *Hyaloperonospora brassicae* to a *Brassica* plant as compared to a plant which may comprise the QTL on chromosome 8, when present in the genome of said *Brassica* plant in combination with the QTL of the invention on chromosome 8 and when both QTLs are homozygously present in said plant. As used herein "the QTL of the invention on chromosome 1" is intended to mean the QTL located on chromosome 1 that can be identified by use of at least one of the markers selected from the group consisting of SEQ ID NOS: 17 to 22, preferably from the group consisting of SEQ ID NOS: 17, 20, 21 and 22. Alternatively, one or more markers for identifying the presence of the QTL on chromosome 1 are selected from the group consisting of SEQ ID NOS: 18, 20 and 21. Alternatively, one or more markers for identifying the presence of the QTL on chromosome 1 are selected from the group consisting of SEQ ID NOS: 17, 18 and 20. Alternatively, one or more markers for identifying the presence of the QTL on chromosome 1 are selected from the group consisting of SEQ ID NOS: 17, 19, 21 and 22. Alternatively, one or more markers for identifying the presence of the QTL on chromosome 1 are selected from the group consisting of SEQ ID NOS: 17, 19 and 22, or any other combination of SEQ ID NOS: 17, 18, 19, 20, 21 and 22, and which confers increased resistance to *Hyaloperonospora brassicae* to a *Brassica* plant as compared to a plant which may comprise the QTL on chromosome 8, when present in the genome of said *Brassica* plant in combination with the QTL of the invention on chromosome 8 and when both QTLs are homozygously present in said plant.

As used herein, the phrase "the QTL on chromosome 8, and optionally the QTL on chromosome 4, and/or the QTL on chromosome 1" is intended to mean that the plant may comprise at least the QTL on chromosome 8 and optionally the QTL on chromosome 4 or may comprise at least the QTL on chromosome 8 and optionally the QTL on chromosome 1, or may comprise the QTL on chromosome 8 and the QTL on chromosome 4 and the QTL on chromosome 1.

As used herein "progeny" is intended to mean the first and all further descendants from a cross with a plant of the invention and having obtained the QTL(s) of the invention therefrom. "Progeny" also encompasses *Brassica* plants that carry the QTL(s) of the invention and have the trait of the invention, and are obtained from other plants, or progeny of plants, of the invention by vegetative propagation or multiplication. Progeny of the invention comprise the QTL on chromosome 8, and optionally the QTL on chromosome 4, and/or the QTL on chromosome 1 and show resistance to *Hyaloperonospora brassicae*.

As used herein "trait" is intended to mean the resistance phenotype of the cultivated *Brassica* plant. In particular, the word "trait" refers to the trait of the invention, more in particular to the resistance or increased resistance to *Hyaloperonospora brassicae*. When a cultivated *Brassica* plant exhibits the trait of the invention, its genome may comprise the QTL on chromosome 8, and optionally the QTL on chromosome 4 and/or the QTL on chromosome 1 causing the trait of the invention. The cultivated *Brassica* plant thus may comprise the QTL(s) of the invention. Hence, the "trait of the invention" or "phenotype of the invention" as used herein is intended to refer to the trait of resistance to *Hyaloperonospora brassicae*.

As used herein, "plant of the invention" is defined as a *Brassica* plant, preferably a *Brassica oleracea* plant, that is resistant to *Hyaloperonospora brassicae* as described herein. The plant of the invention may comprise the QTL of the invention on chromosome 8, and optionally the QTL of the invention on chromosome 4 and/or the QTL of the invention on chromosome 1 which confer resistance to the *Hyaloperonospora brassicae*. In the context of this invention, when referring to a *Brassica* plant, unless otherwise specified, it is a cultivated *Brassica* plant.

In a further aspect of the invention, the plant of the invention which carries the QTL of the invention on chromosome 8, and optionally the QTL of the invention on chromosome 4 and/or the QTL of the invention on chromosome 1 which QTLs confer resistance to the *Hyaloperonospora brassica*, is an agronomically elite *Brassica* plant, preferably an agronomically elite *Brassica oleracea* plant. In the context of this invention, an agronomically elite *Brassica* plant is a plant having a genotype that results into an accumulation of distinguishable and desirable agronomic traits which allow a producer to harvest a product of commercial significance. Preferably the agronomically elite *Brassica* plant of the invention is a plant of an inbred line or a hybrid.

The phrase "present in" may also mean "found in" or "contained in" or "obtainable from" (the genome of) plants grown from seeds of the deposit or the deposited seeds themselves. These phrases are intended to indicate that the QTL of the invention on chromosome 8, and optionally the QTL of the invention on chromosome 4, and/or the QTL of the invention on chromosome 1 is essentially the same or the same as the QTL in the genome of the deposited material. The QTL need not be identical and may comprise polymorphisms (i.e. variation in sequence) as compared to the QTL(s) of the invention, but these polymorphisms do not have any bearing on the function of the QTL in causing the resistance to *Hyaloperonospora brassicae*.

Although the present invention and its advantages have been described in detail, it should be understood that various changes, substitutions and alterations can be made herein without departing from the spirit and scope of the invention as defined in the appended claims.

The present invention will be further elucidated in the Examples that follow. These are provided for illustrative purposes only and are not intended to limit the invention in any way.

EXAMPLES

Example 1

*Hyaloperonospora brassicae* Resistance Testing of *Brassica* Plants

To test whether a *Brassica* plant is resistant to *Hyaloperonospora brassicae*, a bio-assay was performed. About 20 seeds per plots were sown and one row between two plots was left empty. *Brassica* plants were grown under standard Dutch greenhouse conditions at a temperature regime of 15° C./15° C. night/day. At 10 days after sowing the cotyledons were sprayed with the sporangial suspension of "isolate 2". The isolate of *Hyaloperonospora brassicae* was maintained on living *Hyaloperonospora brassicae* susceptible *Brassica* plants. The inoculated cotyledons were incubated under controlled conditions being a 12° C./14° C. night/day regime. Each plant was visually scored according to Table 1 at 7 days and 14 days after inoculation to phenotypically identify *Hyaloperonospora brassicae* resistant *Brassica* plants. This screen identified a number of *Hyaloperonospora brassicae* resistant *Brassica* plants, of which one was selected for further research. The selected plant showed resistance which is represented by a score 1-7 of Table 1.

TABLE 1

Overview of infection symptoms and classification stadia of *Hyaloperonospora brassicae* infected *Brassica* plants (scale 1-9) with grey coloration

| Score | Symptoms | Classification |
| --- | --- | --- |
| 1 | Clean Cotyledons | Resistant |
| 2 | Few necrotic spots | Resistant |
| 3 | Many necrotic spots | Resistant |
| 5 | Single or few spores | Intermediate resistance |
| 7 | Small patches of sporulation | Intermediate resistance |
| 8 | Large patches of sporulation | Susceptible |
| 9 | Much sporulation on both up- and downside of the leaf/cotyledon | Susceptible |

The selected plant was tested in a large screen performed with 42 different *Hyaloperonospora brassicae* isolates (34 isolates were included in the test in 2014 and 14 isolates were included in test in 2017) collected in different locations of the world. Isolate 1, isolate 2, isolate 3 and isolate 10 were also included in the test. The average results for 32 isolates are represented in Table 2. The selected plant of the invention scored resistant against 12 isolates out of the 34 isolates tested in 2014 and it was resistant to 5 isolates out of the 14 isolates tested in 2017. The selected plant further showed intermediate resistance to 17 out of the 34 isolates tested in 2014 and against 4 out of the 14 isolates tested in 2017. Considering that the isolates were collected in very different countries and locations these results show that the plant of the invention has a broad-spectrum resistance.

TABLE 2

Overview of resistance of the plant of the invention to 42 different *Hyaloperonospora brassicae* isolates collected in different countries or locations.

| Isolate name | Country | Location | 2014 | 2017 |
| --- | --- | --- | --- | --- |
| Isolate 1 | The Netherlands | — | Resistant | Resistant |

TABLE 2-continued

Overview of resistance of the plant of the invention to 42 different *Hyaloperonospora brassicae* isolates collected in different countries or locations.

| Isolate name | Country | Location | 2014 | 2017 |
|---|---|---|---|---|
| Isolate 2 | The Netherlands | Fijnaart | Resistant | Resistant |
| Isolate 3 | Germany | Rommelshausen | Intermediate Resistance | Intermediate Resistance |
| Isolate 4 | Ukraine | Kakhovka | Intermediate Resistance | — |
| Isolate 5 | Belgium | Duffel | Intermediate Resistance | — |
| Isolate 6 | Germany | — | Resistant | — |
| Isolate 7 | Spain | — | Resistant | — |
| Isolate 10 | India | Pannipat - Haryana | Intermediate Resistance | Resistant |
| Isolate 11 | India | Punjab - Ludhiana | Intermediate Resistance | — |
| Isolate 12 | Germany | Helserdeich | Resistant | — |
| Isolate 13 | Germany | Helserdeich | Intermediate Resistance | — |
| Isolate 14 | The Netherlands | — | Intermediate Resistance | — |
| Isolate 15 | Spain | La Palma | Resistant | — |
| Isolate 16 | Portugal | Peniche | Resistant | — |
| Isolate 17 | Spain | Murcia | Resistant | — |
| Isolate 18 | Germany | Lüneburg | Resistant | — |
| Isolate 19 | Macedon | Strumitza | Intermediate Resistance | — |
| Isolate 20 | The Netherlands | Fijnaart | Resistant | — |
| Isolate 21 | Spain | Murcia | Intermediate Resistance | — |
| Isolate 22 | Germany | — | Resistant | — |
| Isolate 23 | Germany | Helserdeich | Intermediate Resistance | — |
| Isolate 24 | Turkey | Antalya | Intermediate Resistance | — |
| Isolate 26 | Germany | Albersdorf | Intermediate Resistance | — |
| Isolate 27 | Portugal | — | Intermediate Resistance | — |
| Isolate 28 | The Netherlands | Hem | Intermediate Resistance | — |
| Isolate 29 | Germany | — | Intermediate Resistance | — |
| Isolate 30 | Spain | Murcia | Resistant | — |
| Isolate 31 | Serbia | Leskovacs | Intermediate Resistance | — |
| Isolate 32 | Germany | Pfalz | Intermediate Resistance | — |
| Isolate 33 | Hungary | Felgyö | Intermediate Resistance | — |
| Isolate 40 | India | Punjab - Langrian | — | Intermediate Resistance |
| Isolate 41 | The Netherlands | Fijnaart | — | Resistant |
| Isolate 42 | The Netherlands | Fijnaart | — | Intermediate Resistance |

"—" means that no data is available.
The isolates to which the plant of the invention showed resistance or intermediate resistance in 2014 and/or 2017 are listed.

Example 2

QTL Mapping

In order to map the *Hyaloperonospora brassicae* resistance conferring QTLs of the invention, F2 populations with two different backgrounds and two F3 populations were developed by though backcrossing of an internal susceptible line and the plant selected in Example 1. The *Brassica* plant of the invention is the donor parent for the trait of the invention, whereas the internal susceptible line is the wild type line that does not show resistance to *Hyaloperonospora brassicae*.

A first F2 population was developed with the plant selected in Example 1 and the internal susceptible internal breeding line 2 which is a broccoli plant (*Brassica oleracea* var. *italica* Plenck). 351 F2 plants were used for the mapping with a first *Hyaloperonospora brassicae* isolate (isolate 2). A large number of 823 markers were run on the samples. From these, 729 could be used for mapping as the others were non-polymorphic or otherwise non-informative. The mapping data resulted in the identification of a QTL region on chromosome 8. The same F2 population was used for the mapping with another *Hyaloperonospora brassicae* isolate (isolate 1). For this mapping 750 markers were run on the samples of 250 F2. From these 750 markers, 714 could be used for mapping as the others were non-polymorphic or otherwise non-informative. The data resulted in the identification of QTL regions located on chromosomes 1, 4, and 8. For finemapping, 93 new markers were developed: 29 were located on chromosome 1, 20 new markers located on chromosome 4, and the remaining 44 markers were non-polymorphic.

A second F2 population was developed with the plant selected in Example 1 and the internal susceptible Internal breeding line 1. 240 F2 plants were used for the mapping with a first *Hyaloperonospora brassicae* isolate (isolate 2). A large number of 907 markers were run on the samples. From these, 794 could be used for mapping as the others were non-polymorphic or otherwise non-informative. Mapping of the data resulted in the confirmation of the QTL on chromosome 8. The same F2 population was used for the mapping with another *Hyaloperonospora brassicae* isolate (isolate 1). For this mapping 875 markers were run on the samples of 250 F2 plants. From these 875 markers, 791 could be used for mapping as the others were non-polymorphic or otherwise non-informative. The data confirmed the QTL region on chromosome 8, the QTL on chromosomes 1, and the QTL on chromosome 4. For finemapping this regions 93 new markers were provided: 18 markers were located on chromosome 1 and 60 were located on chromosome 4; the remaining 15 markers were non-polymorphic. The same F2 population was further used for the mapping with a third *Hyaloperonospora brassicae* isolate (isolate 10). 886 markers were run on the samples of 350 F2 plants. 852 makers could be used for mapping as the others were non-polymorphic or otherwise non-informative. The data resulted in the identification of a QTL region on chromosome 8, a QTL region on chromosome 4 and a QTL region on chromosome 1. Each population was tested for resistance to *Hyaloperonospora brassicae* in two assessments 7 and 14 days after infection as described in Example 1. All plants were sampled to obtain DNA. A good linkage map was obtained covering all 9 *Brassica oleracea* chromosomes.

The selected markers located on chromosomes 8, 4, and 1 were confirmed on a F3 line which was obtained by crossing a F2 plant that was tested above with the susceptible internal breeding line 1. 250 F3 plants were tested and 43 markers were run on the samples. From these, 41 could be used for mapping as the others were non-polymorphic or otherwise non-informative. The mapping on the F3 population was performed with three different *Hyaloperonospora brassicae* isolates (isolate 1, isolate 2 and isolate 10).

Phenotypic scores, genotypic data, and the consensus map containing marker positions were used as input data for the QTL mapping. QTL analysis was performed, and mapping of the data resulted in the confirmation of the QTL on chromosome 8, the QTL on chromosome 4 and the QTL on chromosome 1, which were identified in the F2 populations. Polymorphic SNP markers that were identified in this analysis are SEQ ID NOS. 2, 4, 6, 10, 11, 13, 14, 16, 17, 20, 21 and 22 and can be used to detect these QTLs are presented in Table 3.

Further 169 markers were developed in the three QTL regions of interest. These markers were designed to be polymorphic between the plant of the invention and the internal breeding line 1 and the internal breeding line 2. The 169 markers were run on three different F3 inbred populations; a F3 population that segregated only for the QTL on chromosome 8, a F3 population that segregated only for the QTL on chromosome 4 and a F3 population that segregated only for the QTL on chromosome 1. The three F3 populations were tested with the *Hyaloperonospora brassicae* isolate 2. The 169 markers were also run on the internal breeding line 1 and the internal breeding line 2. 150 makers out of the 169 could be used as the others were non-polymorphic or otherwise non-informative. Markers that were polymorphic between the plant of the invention and the internal breeding line 1 and/or the internal breeding line 2 and linked to the resistance *Hyaloperonospora brassicae* were selected. Polymorphic SNP markers that were selected in this analysis are SEQ ID Nos 1, 3, 5, 7, 8, 9, 12, 15, 18, and 19.

The sequences of these markers selected on the F2 and F3 plants are given in FIG. 1. These markers can be used to identify the presence of a QTL in plants grown from the deposit. In the seed deposited with the NCIMB under the accession number NCIMB 43346, the *Hyaloperonospora brassicae* resistance is linked to the SNP markers with SEQ ID NOS: 1 to 22. A *Brassica* plant that is part of the invention and may comprise the QTL on chromosome 8 and optionally the QTL on chromosome 4 and/or the QTL on chromosome 1 need not necessarily have all polymorphic SNP markers of SEQ ID NOS: 1 to 22, but the presence of one or more of said markers can be used to identify the presence of the QTL on chromosome 8, 4, or 1.

TABLE 3

Overview of the SNP markers, with the SEQ ID No of the marker sequence that is given in FIG. 1, the chromosome on which the QTL is located, the marker score which is the nucleotide of the SNP of the marker of the invention as represented in the sequence in FIG. 1, the nucleotide of the SNP as found in the wild type allele, as well as the position of the SNP as represented in FIG. 1. The position is based on the public genome *B. oleracea* (chromosome v1.0) 2013-06-08.

| Marker name | QTL on chromo-some | Position of the SNP in the sequence of FIG. 1 | Nucleotide of the SNP in FIG. 1, to be used as marker of the invention | Nucleotide of the SNP in the wild type (susceptible allele) | Physical position (bp) based on the public genome *B. oleracea* v.1.0) | Genetic position (cM) |
|---|---|---|---|---|---|---|
| SEQ ID NO: 1 | 8 | 101 | G | A | 39440170 | 59.36 |
| SEQ ID NO: 2 | 8 | 101 | T | G | 39850302 | 63.3 |
| SEQ ID NO: 3 | 8 | 101 | A | G | 39935677 | 63.8 |
| SEQ ID NO: 4 | 8 | 101 | A | G | 40323443 | 67.13 |
| SEQ ID NO: 5 | 8 | 101 | C | A | 40503456 | 68.54 |
| SEQ ID NO: 6 | 8 | 101 | C | T | 40655304 | 69.68 |
| SEQ ID NO: 7 | 8 | 101 | T | C | 40740232 | 70.29 |
| SEQ ID NO: 8 | 4 | 101 | A | T | 26241676 | 46.65 |
| SEQ ID NO: 9 | 4 | 61 | A | G | 26376528 | 46.36 |
| SEQ ID NO: 10 | 4 | 101 | G | A | 29276663 | 50.12 |
| SEQ ID NO: 11 | 4 | 101 | T | C | 31686360 | 56.65 |
| SEQ ID NO: 12 | 4 | 101 | A | G | 32759365 | 54.2 |
| SEQ ID NO: 13 | 4 | 101 | T | C | 34586700 | 50.42 |
| SEQ ID NO: 14 | 4 | 101 | A | C | 35073096 | 55.26 |
| SEQ ID NO: 15 | 4 | 61 | A | G | 35358564 | 58.92 |
| SEQ ID NO: 16 | 4 | 101 | A | G | 35892628 | 65.76 |
| SEQ ID NO: 17 | 1 | 101 | G | A | 3804227 | 35.17 |
| SEQ ID NO: 18 | 1 | 101 | G | A | 5454818 | 40.13 |
| SEQ ID NO: 19 | 1 | 101 | A | G | 5710923 | 40.59 |
| SEQ ID NO: 20 | 1 | 101 | A | T | 7019434 | 44.51 |

TABLE 3-continued Overview of the SNP markers, with the SEQ ID No of the marker sequence that is given in FIG. 1, the chromosome on which the QTL is located, the marker score which is the nucleotide of the SNP of the marker of the invention as represented in the sequence in FIG. 1, the nucleotide of the SNP as found in the wild type allele, as well as the position of the SNP as represented in FIG. 1. The position is based on the public genome B. oleracea (chromosome v1.0) 2013-06-08.

| Marker name | QTL on chromo-some | Position of the SNP in the sequence of FIG. 1 | Nucleotide of the SNP in FIG. 1, to be used as marker of the invention | Nucleotide of the SNP in the wild type (susceptible allele) | Physical position (bp) based on the public genome B. oleracea v.1.0) | Genetic position (cM) |
|---|---|---|---|---|---|---|
| SEQ ID NO: 21 | 1 | 101 | C | G | 7496629 | 45.72 |
| SEQ ID NO: 22 | 1 | 101 | C | T | 33039781 | 54.72 |

Example 3

Confirmation of the QTLs

The selected *Brassica* plant of Example 1 was crossed with an internal breeding line (internal breeding line 1) which is a cauliflower plant (*Brassica oleracea* var. *botrytis* L.) plant. F1 plants from these crosses were grown and F2 seeds were also obtained. The F2 plants were crossed again with the internal breeding line 1 in order to obtain F3 plants that carried the QTL of the invention on chromosome 8, the QTL of the invention on chromosome 4 and the QTL of the invention on chromosome 1 either homozygously or heterozygously or the plant did not carry the QTL(s) of the invention. A new screen was performed with three different *Hyaloperonospora brassicae* isolates herein called isolate 1, isolate 2 and isolate 3 and the average scores are represented in Table 4. The plants were phenotypically scored with the scores as represented in Table 1, 7 and 14 days after the infection with the *Hyaloperonospora brassicae* isolates.

Plants that do not comprise the QTL on chromosome 8 and the QTL on chromosome 4 or the QTL on chromosome 1 and plants that comprise the QTL on chromosome 4 or the QTL on chromosome 1 heterozygously or homozygously, were susceptible to all three isolates in the two assessments (average scores 8-9). The phenotype of these plants fall under the definition of "susceptible" as described herein.

A higher percentage of plants within a population of plants which may comprise the QTL of the invention on chromosome 8 homozygously and the QTL of the invention on chromosome 4 homozygously or the QTL on chromosome 1 homozygously, showed increased resistance as compared to plants which may comprise only the QTL of the invention on chromosome 8.

A higher percentage of plants within a population of plants which may comprise the QTL of the invention on chromosome 8 homozygously and the QTL on chromosome 4 homozygously and the QTL of the invention on chromosome 1 heterozygously and a higher portion of plants which may comprise the QTL of the invention on chromosome 8 homozygously and the QTL on chromosome 4 heterozygously and the QTL of the invention on chromosome 1 homozygously showed increased resistance as compared to plant which may comprise the QTL of the invention on chromosome 8 homozygously and the QTL of the invention on chromosome 4 or the QTL of the invention on chromosome 1 homozygously.

Plants which may comprise the QTL of the invention on chromosome 8, the QTL of the invention on chromosome 4 and the QTL of the invention on chromosome 1, all three QTLs homozygously showed the highest resistance level.

TABLE 4

Overview of the average resistance levels of plants which may comprise different combinations of the QTL of the invention on chromosome 8 ("QTL on Chr. 8"), the QTL of the invention on chromosome 4 ("QTL on Chr. 4") and the QTL of the invention on chromosome 1 ("QTL on Chr. 1").

| | | | | Isolate 1 | | Isolate 2 | | Isolate 3 | |
|---|---|---|---|---|---|---|---|---|---|
| | QTL on Chr. 8 | QTL on Chr. 4 | QTL on Chr. 1 | (1) | (2) | (1) | (2) | (1) | (2) |
| 1 | — | — | — | 9.0 | 9.0 | 8.7 | 8.7 | 8.8 | 8.8 |
| 2 | — | — | Heterozygous | 9.0 | 9.0 | 8.8 | 8.8 | 9.0 | 9.0 |
| 3 | — | — | Homozygous | 9.0 | 9.0 | 8.9 | 8.9 | 8.7 | 8.7 |
| 4 | — | Heterozygous | — | 8.8 | 8.8 | 8.7 | 8.7 | 8.8 | 8.8 |
| 5 | — | Homozygous | — | 8.8 | 8.8 | 8.6 | 8.6 | 8.8 | 8.8 |
| 6 | — | Heterozygous | Heterozygous | 8.9 | 8.9 | 8.7 | 8.7 | 8.8 | 8.8 |
| 7 | — | Heterozygous | Homozygous | 8.9 | 8.9 | 8.7 | 8.8 | 8.8 | 8.8 |
| 8 | — | Homozygous | Heterozygous | 8.4 | 8.8 | 8.7 | 8.7 | 8.8 | 8.8 |
| 9 | — | Homozygous | Homozygous | 9.0 | 9.0 | 8.8 | 8.8 | 8.7 | 8.7 |
| 10 | Heterozygous | — | — | 8.0 | 8.2 | 7.5 | 8.0 | 6.2 | 7.3 |
| 11 | Heterozygous | — | Heterozygous | 7.9 | 8.2 | 7.7 | 8.1 | 6.3 | 7.4 |
| 12 | Heterozygous | — | Homozygous | 7.8 | 8.1 | 7.1 | 7.8 | 5.8 | 6.9 |
| 13 | Heterozygous | Heterozygous | — | 7.3 | 7.6 | 7.0 | 7.6 | 6.2 | 7.5 |
| 14 | Heterozygous | Homozygous | — | 5.2 | 5.7 | 5.3 | 6.3 | 5.5 | 6.2 |
| 15 | Heterozygous | Heterozygous | Heterozygous | 6.6 | 7.1 | 6.7 | 7.5 | 5.4 | 6.4 |

TABLE 4-continued

Overview of the average resistance levels of plants which may comprise different combinations of the QTL of the invention on chromosome 8 ("QTL on Chr. 8"), the QTL of the invention on chromosome 4 ("QTL on Chr. 4") and the QTL of the invention on chromosome 1 ("QTL on Chr. 1").

|  | QTL on Chr. 8 | QTL on Chr. 4 | QTL on Chr. 1 | Isolate 1 (1) | Isolate 1 (2) | Isolate 2 (1) | Isolate 2 (2) | Isolate 3 (1) | Isolate 3 (2) |
|---|---|---|---|---|---|---|---|---|---|
| 16 | Heterozygous | Heterozygous | Homozygous | 6.3 | 6.8 | 6.5 | 7.4 | 5.6 | 6.5 |
| 17 | Heterozygous | Homozygous | Heterozygous | 5.0 | 5.3 | 5.9 | 6.6 | 5.1 | 6.1 |
| 18 | Heterozygous | Homozygous | Homozygous | 4.8 | 5.4 | 4.9 | 6.3 | 4.6 | 6.6 |
| 19 | Homozygous | — | — | 5.7 | 6.2 | 6.6 | 7.3 | 4.2 | 6.3 |
| 20 | Homozygous | — | Heterozygous | 6.0 | 6.7 | 6.5 | 8.1 | 3.6 | 6.0 |
| 21 | Homozygous | — | Homozygous | 4.1 | 5.1 | 3.9 | 5.5 | 3.2 | 4.1 |
| 22 | Homozygous | Heterozygous | — | 6.9 | 7.5 | 6.4 | 7.6 | 5.5 | 6.6 |
| 23 | Homozygous | Heterozygous | Heterozygous | 4.8 | 5.4 | 4.7 | 5.7 | 3.5 | 4.7 |
| 24 | Homozygous | Heterozygous | Homozygous | 3.5 | 3.9 | 3.1 | 4.2 | 3.2 | 3.9 |
| 25 | Homozygous | Homozygous | — | 4.0 | 4.8 | 4.3 | 5.6 | 4.4 | 6.4 |
| 26 | Homozygous | Homozygous | Heterozygous | 3.1 | 4.1 | 3.4 | 4.7 | 3.7 | 4.4 |
| 27 | Homozygous | Homozygous | Homozygous | 2.2 | 2.7 | 2.9 | 3.8 | 3.1 | 3.8 |

The QTLs are either homozygously, heterozygously or absent ("—").
Two assessments ((1) and (2)) were performed for each of the three *Hyaloperonospora brassicas* isolates (isolate 1, isolate 2 and isolate 3)..

Example 4

*Hyaloperonospora brassicae* resistance testing of *Brassica* plants in a field trial Plants of the invention were compared with susceptible Broccoli plants of the publicly available varieties Green Duke and Lucky, as well as with a broccoli plant of internal breeding line 2 in an open field trial. Plants of the invention are plants of which a representative sample was deposited with the NCIMB under NCIMB accession number 43346. Plants were naturally infected by *Hyaloperonospora brassicae* in 13 different field trials taking place in 3 successive years. Trial 1-12 were done in The Netherlands and trial 13 was done in Spain.

The leaves of each plant were scored based on the scale explained in Table 5. Symptoms were scored when the *Brassica* plants were mature in harvestable stage. The average scores for the evaluation on the leaves (Table 5) of the tested plants are represented in Table 6 and show that the plants of the invention were resistant to *Hyaloperonospora brassicae* in all the 13 trials. In trial number 13 the plants of the invention showed intermediate resistance. In all the trials the susceptible control plants had an average score which was higher than the one of the plant of the invention.

TABLE 5

Overview of infection symptoms on the leaves and classification stadia of *Hyaloperonospora brassicae* infected *Brassica* plants (scale 1-9)

| Score | Symptoms | Classification |
|---|---|---|
| 1 | No symptoms | Resistant |
| 3 | Small spots and hardly sporulation | Resistant |
| 5 | Clear symptoms up to 10% on the old leaves surface, with clear sporulation | Intermediate resistance |
| 7 | Clear symptoms and more than 10% of leave surface infected | Susceptible |
| 9 | Lot of symptoms/extreme yellowing and sporulation | Susceptible |

TABLE 6

Results of the *Hyaloperonospora brassicae* resistance testing of *Brassica* plants in field trials (scoring of the leaves)

| | Trials | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Plant of the invention | 1 | 1 | 3 | 3 | 1 | 1 | 1 | 1 | 1 | 3 | 1 | 1 | 5 |
| Green Duke | 9 | 9 | 9 | 9 | 9 | 9 | 9 | — | — | — | — | — | — |
| Internal breeding line 2 | 3 | 7 | 5 | 7 | 7 | 7 | 7 | 3 | 7 | 7 | 7 | 7 | — |
| Lucky | 9 | 9 | 9 | 9 | 9 | 9 | 7 | 5 | 7 | 9 | 9 | 9 | — |

The invention is further described by the following numbered paragraphs:

1. A *Brassica* plant, in particular a *Brassica oleracea* plant, that is resistant to *Hyaloperonospora brassicae*, comprising a QTL on chromosome 8 which confers resistance to *Hyaloperonospora brassicae* to the *Brassica* plant.

2. The *Brassica* plant of numbered paragraph 1, wherein the resistance is detectable in the cotyledon stage.

3. The *Brassica* plant of numbered paragraph 1 or 2, wherein the QTL on chromosome 8 is located between SEQ ID NOS: 1 and 7.

4. The *Brassica* plant of numbered paragraphs 1 to 3, wherein the presence of the QTL on chromosome 8 can be identified by use of at least one of the markers selected from the group consisting of SEQ ID NOS: 1 to 7.

5. The *Brassica* plant of any one of the numbered paragraphs 1 to 4, wherein the QTL on chromosome 8 is as comprised in the genome of a *Brassica* plant representative seed of which was deposited with the NCIMB under accession number NCIMB 43346.

6. The *Brassica* plant of any one of the numbered paragraphs 1 to 5, further comprising a QTL on chromosome 4.

7. The *Brassica* plant of numbered paragraph 6, wherein the QTL on chromosome 4 is located between SEQ ID NOS: 8 and 16.

8. The *Brassica* plant as claimed in numbered paragraph 6 or 7, wherein the presence of the QTL on chromosome 4 can be identified by use of at least one of the markers selected from the group consisting of SEQ ID NOS: 8 to 16.

9. The *Brassica* plant of any one of the numbered paragraphs 6 to 8, wherein the QTL on chromosome 4 is as comprised in the genome of a *Brassica* plant representative seed of which was deposited with the NCIMB under accession number NCIMB 43346.

10. The *Brassica* plant of any one of the numbered paragraphs 1 to 9, further comprising a QTL on chromosome 1.

11. The *Brassica* plant of numbered paragraph 10, wherein the QTL on chromosome 1 is located between SEQ ID NOS: 17 and 22.

12. The *Brassica* plant of numbered paragraph 10 or 11, wherein the presence of the QTL on chromosome 1 can be identified by use of at least one of the markers selected from the group consisting of SEQ ID NOS: 17 to 22.

13. The *Brassica* plant of any one of the numbered paragraphs 10 to 12, wherein the QTL on chromosome 1 is as comprised in the genome of a *Brassica* plant representative seed of which was deposited with the NCIMB under accession number NCIMB 43346.

14. The *Brassica* plant of any one of the numbered paragraphs 6 to 13, wherein when the QTLs are homozygously present the plant has an increased resistance to *Hyaloperonospora brassicae* as compared to the resistance to *Hyaloperonospora brassicae* of a *Brassica* plant comprising only the QTL on chromosome 8.

15. The *Brassica* plant of any one of the numbered paragraphs 10 to 13, wherein when the QTL on chromosome 8 is homozygously present and the QTL on chromosome 4 and the QTL on chromosome 1 is homozygously present, the plant has an increased resistance to *Hyaloperonospora brassicae* as compared to the resistance to *Hyaloperonospora brassicae* of a *Brassica* plant comprising the QTL on chromosome 8 and the QTL on chromosome 4 or the QTL on chromosome 1.

16. A *Brassica* seed comprising the QTL on chromosome 8 and optionally the QTL on chromosome 4 and/or the QTL on chromosome 1, wherein the QTLs are as defined in any one of the numbered paragraphs 1 to 13.

17. The *Brassica* seed of numbered paragraph 16, wherein a plant grown from said seed shows resistance to *Hyaloperonospora brassicae*.

18. A progeny plant of the *Brassica* plant of any one of the numbered paragraphs 1 to 15, or progeny of a plant grown from seed as claimed in numbered paragraph 16 or claim 17, wherein the plant comprises the QTL on chromosome 8 and optionally the QTL on chromosome 4 and/or the QTL on chromosome 1, wherein the QTLs are as defined in any one of the numbered paragraphs 1 to 13.

19. The progeny plant of numbered paragraph 18, wherein the progeny plant shows resistance to *Hyaloperonospora brassicae*.

20. Propagation material derived from a plant of any one of the numbered paragraphs 1 to 15, or from progeny of a plant grown from seed as claimed in numbered paragraph 16 or numbered paragraph 17, wherein the propagation material is suitable for sexual reproduction, and is in particular selected from the group consisting of a microspore, pollen, an ovary, an ovule, an embryo sac, and an egg cell; microspore, pollen, an ovary, an ovule, an embryo sac, and an egg cell; or is suitable for vegetative reproduction, and is in particular selected from the group consisting of a cutting, a root, a stem, a cell, and a protoplast; or is suitable for tissue culture of regenerable cells, and is in particular selected from the group consisting of a leaf, pollen, an embryo, a cotyledon, a hypocotyl, a meristematic cell, a root, a root tip, an anther, a flower, a seed, and a stem, and wherein the propagation material comprises the QTL on chromosome 8 and optionally the QTL on chromosome 4 and/or the QTL on chromosome 1, wherein the QTLs are as defined in any one of the numbered paragraphs 1 to 13.

21. Propagation material capable of growing into a plant of any one of the numbered paragraphs 1 to 15, wherein the propagation material is suitable for sexual reproduction, and is in particular selected from the group consisting of a microspore, pollen, an ovary, an ovule, an embryo sac; and an egg cell; or is suitable for vegetative reproduction, and is in particular selected from the group consisting of a cutting, a root, a stem, a cell, and a protoplast; or is suitable for tissue culture of regenerable cells, and is in particular selected from the group consisting of a leaf, pollen, an embryo, a cotyledon, a hypocotyl, a meristematic cell, a root, a root tip, an anther, a flower, a seed, and a stem, and wherein the propagation material comprises the QTL on chromosome 8 and optionally the QTL on chromosome 4 and/or the QTL on chromosome 1, wherein the QTLs are as defined in any one of the numbered paragraphs 1 to 13.

22. A cell of a resistant *Brassica* plant showing resistance to *Hyaloperonospora brassicae*, which cell comprises the QTL on chromosome 8 and optionally the QTL on chromosome 4 and/or the QTL on chromosome 1, wherein the QTLs are as defined in any one of the numbered paragraphs 1 to 13.

23. A tissue culture of a *Brassica* plant shows resistance to *Hyaloperonospora brassicae*, that can be regenerated into a *Brassica* plant with shows resistance to *Hyaloperonospora brassicae*, which tissue culture comprises the QTL on chromosome 8 and optionally the QTL on chromosome 4 and/or the QTL on chromosome 1, wherein the QTLs are as defined in any one of the numbered paragraphs 1 to 13.

24. A tissue culture of regenerable cells or protoplasts obtained from the *Brassica* plant of any one of the numbered paragraphs 1 to 15, 18 or 19, wherein the tissue culture can be derived from a leave, pollen, embryo, cotyledon, hypocotyl, meristematic cell, root tip, anther, flower, seed or stem.

25. Harvested part of a *Brassica* plant of any one of the numbered paragraphs 1 to 15, 18 or 19, which is in particular selected from the group consisting of cabbage head, curd, stem, leaf, sprout, and seed, optionally in processed form.

26. The harvested part of numbered paragraph 25, wherein the harvested part is a food product.

27. A marker for the identification of the on chromosome 8 which when present in the genome of a *Brassica* plant confers resistance to *Hyaloperonospora brassicae*, which marker is selected from the group consisting of SEQ ID NOS: 1 to 7.

28. A marker for the identification of the QTL on chromosome 4 which when homozygously present in combination with the QTL on chromosome 8, as defined in numbered paragraph 27, in the genome of a *Brassica* plant confers an increased *Hyaloperonospora brassicae* resistance to a plant as compared to the resistance to *Hyaloperonospora brassicae* of a *Brassica* plant comprising only the QTL on chromosome 8, which marker is selected from the group consisting of SEQ ID NOS: 8 to 16.

29. A marker for the identification of the QTL on chromosome 1 which when homozygously present in combination with the QTL on chromosome 8, as defined in numbered paragraph 27, in the genome of a *Brassica* plant confers an increased *Hyaloperonospora brassicae* resistance to a plant as compared to the resistance to *Hyaloperonospora brassicae* of a *Brassica* plant comprising only the QTL on chromosome 8, which marker is selected from the group consisting of SEQ ID NOS: 17 to 22.

30. Use of the markers as claimed in any one of the numbered paragraphs 27 to 29, to identify and/or develop a *Brassica* plant showing resistance to *Hyaloperonospora brassicae*, and/or develop additional marker(s) linked to the QTL on chromosome 8, the QTL on chromosome 4 and/or the Q11, on chromosome 1.

31. A method of selecting a *Brassica* plant showing resistance to *Hyaloperonospora brassicae*, comprising identifying the presence of the QTL on chromosome 8, and optionally the QTL on chromosome 4 and/or the QTL on chromosome 1, and selecting a plant that comprises the QTL on chromosome 8, and optionally the QTL on chromosome 4 and/or the QTL on chromosome 1 as a *Brassica* plant showing resistance to *Hyaloperonospora brassicae*.

32. The method as claimed in numbered paragraph 31, wherein identifying the presence of the QTL on chromosome 8 is done using a marker selected from the group consisting of SEQ ID NOS: 1 to 7; identifying the presence of the QTL on chromosome 4 is done using a marker selected from the group consisting of SEQ ID NOS: 8 to 16; and identifying the presence of the QTL on chromosome 1 is done using a marker selected from the group consisting of SEQ ID NOS: 17 to 22.

A method for producing a *Brassica* plant showing resistance to *Hyaloperonospora brassicae Hyaloperonospora brassicae*, said method comprising
a) crossing a plant of any one of the numbered paragraphs 1 to 15 with another plant to obtain an F1 population;
b) optionally performing one or more rounds of selling and/or crossing a plant from the F1 to obtain a further generation population;
c) selecting from the further generation population a plant that comprises the QTL on chromosome 8, and optionally the QTL on chromosome 4 and/or the QTL on chromosome 1, and which shows resistance to *Hyaloperonospora brassicae*.

34. The method of numbered paragraph 33, wherein selection of a plant comprising the QTL on chromosome 8, and optionally the QTL on chromosome 4 and/or the QTL on chromosome 1, is suitably done by using a molecular marker selected of the group consisting of SEQ ID NOS: 1 to 7 for the identification of the QTL on chromosome 8; or from the group consisting of SEQ ID NOS: 8 to 16 for the identification of the QTL on chromosome 4; or from the group consisting of SEQ ID NOS: 17 to 22 for the identification of the QTL on chromosome 1.

35. The method of numbered paragraph 33, wherein the plant of any one of the numbered paragraphs 1 to 15 in step a) is a plant grown from seed deposited with the NCIMB under accession number NCIMB 43346.

36. Method for producing a *Brassica* plant showing resistance to *Hyaloperonospora brassicae*, comprising introducing the QTL on chromosome 8 and optionally the QTL on chromosome 4 and/or the QTL on chromosome 1, wherein the QTLs are as defined in any one of the numbered paragraphs 1 to 13, in a *Brassica* plant.

37. A method for selecting a *Brassica* plant or *Brassica* seed for resistance to *Hyaloperonospora brassicae* comprising:
a) assaying genomic nucleic acids of *Brassica* plant or *Brassica* seed for the presence of a genomic *Hyaloperonospora brassicae* resistance marker genetically linked to the QTL on chromosome 8 as defined in any one of the numbered paragraphs 1-5, and optionally the QTL on chromosome 4 as defined in any one of the numbered paragraphs 6-9 and/or the QTL on chromosome 1 as defined in any one of the numbered paragraphs 10-13, said genomic *Hyaloperonospora brassicae* resistance marker being within at least 30 cM, 20 cM, 15 cM, 10 cM, 5 cM or 1 cM of any of SEQ ID NOS: 1 to 22;
b) determining whether said genomic *Hyaloperonospora brassicae* resistance marker is homozygous or heterozygous; and
c) selecting said *Brassica* plant or *Brassica* seed based on said determination.

38. The method of numbered paragraph 37, wherein said genomic *Hyaloperonospora brassicae* resistance marker is associated with *Hyaloperonospora brassicae* resistance genomic region located on chromosome 8 identifiable using SEQ ID NOS: 1 to 7, or complements thereof.

39. The method as of numbered paragraph 38, wherein said *Hyaloperonospora brassicae* resistance marker can be monitored by assaying for an allele of 1, 2, 3, 4, 5, 6, 7, or more markers of SEQ ID No: 1 through SEQ ID No: 7, or complements thereof.

40. The method of numbered paragraph 37, wherein said genomic *Hyaloperonospora brassicae* resistance marker is associated with *Hyaloperonospora brassicae* resistance genomic region located on chromosome 4 identifiable using SEQ ID NOS: 8 to 16, or complements thereof.

41. The method of numbered paragraph 40, wherein said *Hyaloperonospora brassicae* resistance marker can be monitored by assaying for an allele of 1, 2, 3, 4, 5, 6, 7, 8, or more markers of SEQ II) No: 8 through SEQ ID No: 16, or complements thereof.

42. The method of numbered paragraph 37, wherein said genomic *Hyaloperonospora brassicae* resistance marker is associated with *Hyaloperonospora brassicae* resistance genomic region located on chromosome 1 identifiable using SEQ ID NO: 17 to 22, or complements thereof.

43. The method of numbered paragraph 42, wherein said *Hyaloperonospora brassicae* resistance marker can be monitored by assaying for an allele of 1, 2, 3, 4, 5, or more markers of SEQ ID No: 17 through SEQ ID No: 22, or complements thereof.

44. The method of any one of the numbered paragraphs 37 to 43, further comprising obtaining DNA from said *Brassica* plant or seed using a non-destructive method.

45. A method for production of a plant having *Hyaloperonospora brassicae* resistance comprising the steps of:
    a) introducing a mutation in a population of plants;
    b) selecting a *Brassica* plant showing resistance to *Hyaloperonospora brassicae*; resistance
    c) assaying genomic nucleic acids of the plant selected under b) for the presence of a genomic *Hyaloperonospora brassicae* resistance marker genetically linked the QTL on chromosome 8 as defined in any one of the numbered paragraphs 1-5, and optionally the QTL on chromosome 4 as defined in any one of the numbered paragraphs 6-9 and/or the QTL on chromosome 1 as defined in any one of the numbered paragraphs 10-13, which confer the resistance to *Hyaloperonospora brassicae* to the *Brassica* plant, said *Hyaloperonospora brassicae* resistance marker being within at least 30 cM, 20 cM, 15 cM, 10 cM, 5 cM or 1 cM of any of the SEQ ID Nos: 1 to 22 and
    d) growing or cultivating the plants obtained under c).

46. A method for the identification of molecular markers indicative of *Hyaloperonospora brassicae* resistance of a *Brassica* plant, comprising:
    a) isolating DNA from said plant and from a susceptible wild type plant;
    b) screening for molecular markers in a region of said DNA sequence corresponding to any of the SEQ ID Nos: 1 to 22; and
    c) determining co-inheritance of said markers from the wild type plant to said plant.

47. A molecular marker detectable by method of numbered paragraph 46.

48. Use of the molecular marker of numbered paragraph 47 for the selection of a *Brassica* plant.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An agronomically elite *Brassica oleracea* plant, wherein:
said agronomically elite *Brassica oleracea* plant is resistant to *Hyaloperonospora brassicae*,
the resistance is detectable in the cotyledon stage,
said agronomically elite *Brassica oleracea* plant comprising:
a QTL on chromosome 8 between SEQ ID NOS: 1 and 7, which confers resistance to *Hyaloperonospora brassicae* to the *Brassica oleracea* plant,
or
(ii) a QTL on chromosome 8 between SEQ ID NOS: 1 and 7, and a QTL on chromosome 4 located between SEQ ID NOS: 8 and 16, which confers resistance to *Hyaloperonospora brassicae* to the *Brassica oleracea* plant,
or
(iii) a QTL on chromosome 8 between SEQ ID NOS: 1 and 7, and a QTL on chromosome 1 located between SEQ ID NOS: 17 and 22, which confers resistance to *Hyaloperonospora brassicae* to the *Brassica oleracea* plant,
or
(iv) a QTL on chromosome 8 between SEQ ID NOS: 1 and 7, and a QTL on chromosome 4 located between SEQ ID NOS: 8 and 16, and a QTL on chromosome 1 located between SEQ ID NOS: 17 and 22, which confers resistance to *Hyaloperonospora brassicae* to the *Brassica oleracea* plant,
and
the QTL on chromosome 8, the QTL on chromosome 4, and the QTL on chromosome 1 each is as comprised in the genome of a *Brassica oleracea* plant, representative seed of which was deposited with the NCIMB under accession number NCIMB 43346.

2. The agronomically elite *Brassica oleracea* plant of claim 1, comprising (i), the QTL on chromosome 8.

3. The agronomically elite *Brassica oleracea* plant of claim 1, comprising (ii), the QTLs on chromosome 8 and 4.

4. The agronomically elite *Brassica oleracea* plant of claim 1, comprising (iii), the a QTLs on chromosomes 8 and 1.

5. The agronomically elite *Brassica oleracea* plant of claim 1, comprising (iv), the QTLs on chromosomes 8, 4 and 1.

6. The agronomically elite *Brassica oleracea* plant of claim 2 which is broccoli, cauliflower, romanesco, red cabbage, white cabbage, savoy cabbage or kohlrabi.

7. The agronomically elite *Brassica oleracea* plant of claim 3, which is broccoli, cauliflower, romanesco, red cabbage, white cabbage, savoy cabbage or kohlrabi.

8. The agronomically elite *Brassica oleracea* plant of claim 4, which is broccoli, cauliflower, romanesco, red cabbage, white cabbage, savoy cabbage or kohlrabi.

9. The agronomically elite *Brassica oleracea* plant of claim 5, which is broccoli, cauliflower, romanesco, red cabbage, white cabbage, savoy cabbage or kohlrabi.

10. The agronomically elite *Brassica oleracea* plant of claim 3, wherein when the QTL[s] on chromosome 8 is homozygously present and the QTL on chromosome 4 is homozygously present.

11. The agronomically elite *Brassica oleracea* plant of claim 5, wherein the QTL on chromosome 8 is homozygously present and the QTL on chromosome 4 is homozygously present and the QTL on chromosome 1 is homozygously present.

12. An agronomically elite *Brassica oleracea* seed comprising:
   (i) a QTL on chromosome 8 between SEQ ID NOS: 1 and 7, which confers resistance to *Hyaloperonospora brassicae* to the *Brassica oleracea* plant,
   or
   (ii) a QTL on chromosome 8 between SEQ ID NOS: 1 and 7, and a QTL on chromosome 4 located between SEQ ID NOS: 8 and 16, which confers resistance to *Hyaloperonospora brassicae* to the *Brassica oleracea* plant,
   or
   (iii) a QTL on chromosome 8 between SEQ ID NOS: 1 and 7, and a QTL on chromosome 1 located between SEQ ID NOS: 17 and 22, which confers resistance to *Hyaloperonospora brassicae* to the *Brassica oleracea* plant,
   or
   (iv) a QTL on chromosome 8 between SEQ ID NOS: 1 and 7, and a QTL on chromosome 4 located between SEQ ID NOS: 8 and 16, and a QTL on chromosome 1 located between SEQ ID NOS: 17 and 22, which confers resistance to *Hyaloperonospora brassicae* to the *Brassica oleracea* plant,
   wherein:
      said agronomically elite *Brassica oleracea* seed gives rise to a plant that is resistant to *Hyaloperonospora brassicae*,
         the resistance is detectable in the cotyledon stage, and
      the QTL on chromosome 8, the QTL on chromosome 4, and the QTL on chromosome 1 each is as comprised in the genome of a *Brassica oleracea* plant, representative seed of which was deposited with the NCIMB under accession number NCIMB 43346.

13. The *Brassica oleracea* seed of claim 12, wherein the *Brassica oleracea* is broccoli, cauliflower, romanesco, red cabbage, white cabbage, savoy cabbage or kohlrabi.

14. A propagation material derived from the plant of claim 1, wherein the propagation material is suitable for sexual reproduction, and comprises a microspore, pollen, an ovary, an ovule, an embryo sac, or an egg cell; or the propagation material is suitable for vegetative reproduction, and comprises a cutting, a root, a stem, a cell, or a protoplast; or the propagation material is suitable for tissue culture of regenerable cells, and comprises—a leaf, pollen, an embryo, a cotyledon, a hypocotyl, a meristematic cell, a root, a root tip, an anther, a flower, a seed, or a stem; or the propagation material comprises a leaf, pollen, an embryo, a cotyledon, a hypocotyl, a meristematic cell, a root, a root tip, an anther, a flower, a seed, or a stem, and wherein the propagation material comprises the QTL on chromosome 8, or the QTLs on chromosomes 8 and 4, or the QTLs on chromosomes 8 and 1, or the QTLs on chromosomes 8, 4 and 1.

15. A cell or tissue culture of the agronomically elite *Brassica oleracea* plant of claim 1.

16. A harvested part of the *Brassica oleracea* plant of claim 1.

17. A harvested part of the *Brassica oleracea* plant of claim 16 comprising cabbage head, curd, stem, leaf, sprout, or seed.

18. The harvested part of claim 16, wherein the harvested part is a food product.

19. A method of selecting an agronomically elite *Brassica oleracea* plant showing resistance to *Hyaloperonospora brassicae*, comprising identifying the presence of a QTL on chromosome 8, or identifying the presence a QTL on chromosome 8 and the presence of a QTL on chromosome 4 or identifying the presence of a QTL on chromosome 8 and the presence of a QTL on chromosome 1, or identifying the presence of a QTL on chromosome 8 and the presence of a QTL on chromosome 4 and the presence of a QTL on chromosome 1, and selecting a plant that comprises the QTL on chromosome 8, or the QTLs on chromosomes 8 and 4, or the QTLs on chromosomes on 8 and 1, or QTLs on chromosome 8, 4 and 1 as a *Brassica oleracea* plant showing resistance to *Hyaloperonospora brassicae*, wherein identifying the presence of the QTL on chromosome 8 is done using a marker comprising any one of SEQ ID NOS: 1 to 7; identifying the presence of the QTL on chromosome 4 is done using a marker comprising any one of SEQ ID NOS: 8 to 16; and identifying the presence of the QTL on chromosome 1 is done using a marker comprising any one of SEQ ID NOS; 17 to 22.

20. A method for producing an agronomically elite *Brassica oleracea* plant showing resistance to *Hyaloperonospora brassicae*, said method comprising:
   a) crossing the plant of claim 1 with another plant to obtain an F1 population;
   b) optionally performing one or more rounds of selfing and/or crossing with a plant from the F1 population to obtain a further generation population;
   c) selecting from the further generation population, a plant that comprises the QTL on chromosome 8, or a plant that comprises the QTLs on chromosomes 8 and 4, or a plant that comprises the QTLs on chromosomes 8 and 1, or a plant that comprises the QTLs on chromosomes 8, 4 and 1.

21. The method of claim 20, wherein
selecting the plant that comprises the QTL on chromosome 8 is by using a molecular marker comprising any one of SEQ ID NOS: 1 to 7 for the identification of the QTL on chromosome 8; or
selecting the plant that comprises the QTL on chromosome 8 and the QTL on chromosome 4 is by using a molecular marker comprising any one of SEQ ID NOS: 1 to 7 for the identification of the QTL on chromosome 8, and by using a molecular marker comprising any one of SEQ ID NOS: 8 to 16 for the identification of the QTL on chromosome 4; or
selecting the plant that comprises the QTL on chromosome 8 and the QTL on chromosome 1 is by using a molecular marker comprising any one of SEQ ID NOS: 1 to 7 for the identification of the QTL on chromosome 8, and by using a molecular marker comprising any one of SEQ ID NOS: 17 to 22 for the identification of the QTL on chromosome 1; or
selecting the plant that comprises the QTL on chromosome 8 and the QTL on chromosome 4 and the QTL on chromosome 1 is by using a molecular marker comprising any one of SEQ ID NOS: 1 to 7 for the identification of the QTL on chromosome 8, and by using a molecular marker comprising any one of SEQ ID NOS: 8 to 16 for the identification of the QTL on chromosome 4, and by using a molecular marker comprising any one of SEQ ID NOS: 17 to 22 for the identification of the QTL on chromosome 1.

22. The method of claim 20, wherein the plant in step a) is a plant grown from seed deposited with the NCIMB under accession number NCIMB 43346.

23. A method for producing an agronomically elite *Brassica oleracea* plant showing resistance to *Hyaloperonospora brassicae*, comprising introducing a QTL on chromosome 8, or a QTL on chromosome 8 and QTL on chromosome 4, or a QTL on chromosome 8 and a QTL on chromosome 1, or a QTL on chromosome 8 and QTL on chromosome 4 and a QTL on chromosome 1, as comprised in the genome of a *Brassica oleracea* plant, representative seed of which was deposited with the NCIMB under accession number NCIMB 43346.

24. A method for production of an agronomically elite *Brassica oleracea* plant having *Hyaloperonospora brassicae* resistance comprising the steps of:
   a) introducing a mutation in a population of agronomically elite *Brassica oleracea* plants;
   b) selecting a *Brassica oleracea* plant showing resistance to *Hyaloperonospora brassica*;
   c) assaying genomic nucleic acids of the plant selected under b) for the presence of a genomic *Hyaloperonospora brassicae* resistance marker genetically linked to the QTL on chromosome 8, or for the presence of a genomic *Hyaloperonospora brassicae* resistance marker genetically linked to the QTLs on chromosomes 8 and 4, or for the presence of a genomic *Hyaloperonospora brassicae* resistance marker genetically linked to the QTLs on chromosomes 8 and 1, or for the presence of a genomic *Hyaloperonospora brassicae* resistance marker genetically linked to the QTLs on chromosomes 8, 4 and 1, as defined in claim 1, said *Hyaloperonospora brassicae* resistance marker comprises SEQ ID NO: 1-7 for QTL 8, SEQ ID NO: 8-16 for QTL4, and SEQ ID NO: 17-22 for QTL1; and
   d) growing or cultivating the plants obtained under c).

25. The agronomically elite *Brassica oleracea* seed of claim 12, comprising (i), the QTL on chromosome 8.

26. The agronomically elite *Brassica oleracea* seed of claim 12, comprising (ii), the QTLs on chromosomes 8, and 4.

27. The agronomically elite *Brassica oleracea* seed of claim 12, comprising (iii), the QTLs on chromosomes 8, and 1.

28. The agronomically elite *Brassica oleracea* seed of claim 12, comprising (iv), the QTLs on chromosomes 8, 4, and 1.

29. The agronomically elite *Brassica oleracea* seed of claim 25, which is broccoli, cauliflower, romanesco, red cabbage, white cabbage, savoy cabbage or kohlrabi seed.

30. The agronomically elite *Brassica oleracea* seed of claim 26, which is broccoli, cauliflower, romanesco, red cabbage, white cabbage, savoy cabbage or kohlrabi seed.

31. The agronomically elite *Brassica oleracea* seed of claim 27, which is broccoli, cauliflower, romanesco, red cabbage, white cabbage, savoy cabbage or kohlrabi seed.

32. The agronomically elite *Brassica oleracea* seed of claim 28, which is broccoli, cauliflower, romanesco, red cabbage, white cabbage, savoy cabbage or kohlrabi seed.

33. The agronomically elite *Brassica oleracea* plant of claim 1, wherein the plant is a plant of an inbred line, a hybrid, a doubled haploid, or a plant of a segregated population.

34. The agronomically elite *Brassica oleracea* plant of claim 2, wherein the plant is a plant of an inbred line, a hybrid, a doubled haploid, or a plant of a segregated population.

35. The agronomically elite *Brassica oleracea* plant of claim 3, wherein the plant is a plant of an inbred line, a hybrid, a doubled haploid, or a plant of a segregated population.

36. The agronomically elite *Brassica oleracea* plant of claim 4 wherein the plant is a plant of an inbred line, a hybrid, a doubled haploid, or a plant of a segregated population.

37. The agronomically elite *Brassica oleracea* plant of claim 5 wherein the plant is a plant of an inbred line, a hybrid, a doubled haploid, or a plant of a segregated population.

38. The agronomically elite *Brassica oleracea* plant of claim 6 which is broccoli.

39. The agronomically elite *Brassica oleracea* plant of claim 6 which is cauliflower.

40. The agronomically elite *Brassica oleracea* seed of claim 29, which is broccoli seed.

41. The agronomically elite *Brassica oleracea* seed of claim 29, which is cauliflower seed.

* * * * *

UNITED STATES PATENT AND TRADEMARK OFFICE
CERTIFICATE OF CORRECTION

PATENT NO. : 12,054,728 B2
APPLICATION NO. : 17/482624
DATED : August 6, 2024
INVENTOR(S) : Mathieu Pierre Bertrand Detavernier et al.

Page 1 of 1

It is certified that error appears in the above-identified patent and that said Letters Patent is hereby corrected as shown below:

On the Title Page

The Foreign Application Priority Data should be listed as:
(30) Foreign Application Priority Data
Mar. 26, 2019 (WO) PCT/EP2019/057542
Apr. 24, 2019 (WO) PCT/EP2019/060512

In the Claims

Claim 14 should read as:
14. A propagation material derived from the plant of claim 1, wherein the propagation material is suitable for sexual reproduction, and comprises a microspore, pollen, an ovary, an ovule, an embryo sac, or an egg cell; or the propagation material is suitable for vegetative reproduction, and comprises a cutting, a root, a stem, a cell, or a protoplast; or the propagation material is suitable for tissue culture of regenerable cells, and comprises a leaf, pollen, an embryo, a cotyledon, a hypocotyl, a meristematic cell, a root, a root tip, an anther, a flower, a seed, or a stem; or the propagation material comprises a leaf, pollen, an embryo, a cotyledon, a hypocotyl, a meristematic cell, a root, a root tip, an anther, a flower, a seed, or a stem, and wherein the propagation material comprises the QTL on chromosome 8, or the QTLs on chromosomes 8 and 4, or the QTLs on chromosomes 8 and 1, or the QTLs on chromosomes 8, 4 and 1.

Signed and Sealed this
Twenty-ninth Day of April, 2025

Coke Morgan Stewart
*Acting Director of the United States Patent and Trademark Office*